US010368826B2

(12) United States Patent
Tamura et al.

(10) Patent No.: US 10,368,826 B2
(45) Date of Patent: Aug. 6, 2019

(54) RADIANT RAY GENERATION CONTROL APPARATUS, RADIATION IMAGING SYSTEM, AND METHOD FOR CONTROLLING THE SAME

(71) Applicant: CANON KABUSHIKI KAISHA, Tokyo (JP)

(72) Inventors: Toshikazu Tamura, Utsunomiya (JP); Taro Hiroike, Yamato (JP); Tadahiko Iijima, Yokohama (JP); Hirokazu Ohguri, Funabashi (JP); Toshiya Ishioka, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 607 days.

(21) Appl. No.: 15/048,758

(22) Filed: Feb. 19, 2016

(65) Prior Publication Data
US 2016/0174350 A1 Jun. 16, 2016

Related U.S. Application Data

(63) Continuation of application No. 13/865,618, filed on Apr. 18, 2013, now abandoned.

(30) Foreign Application Priority Data

Apr. 19, 2012 (JP) .................. 2012-096094
Apr. 19, 2012 (JP) .................. 2012-096095
(Continued)

(51) Int. Cl.
*A61B 6/00* (2006.01)
*H05G 1/30* (2006.01)
(Continued)

(52) U.S. Cl.
CPC ............... *A61B 6/542* (2013.01); *A61B 6/42* (2013.01); *A61B 6/4208* (2013.01);
(Continued)

(58) Field of Classification Search
CPC ....... A61B 6/42; A61B 6/4233; A61B 6/4411; A61B 6/54; A61B 6/542; A61B 6/548;
(Continued)

(56) References Cited

U.S. PATENT DOCUMENTS 6,885,869 B2 4/2005 Raith
7,015,478 B2 3/2006 Yamamoto
(Continued)

FOREIGN PATENT DOCUMENTS

CN 2462494 Y 11/2001
CN 1573534 A 2/2005
(Continued)

*Primary Examiner* — Allen C. Ho
(74) *Attorney, Agent, or Firm* — Canon USA Inc., IP Division

(57) ABSTRACT

A radiation imaging control apparatus includes an exposure switch configured to instruct radiation emission, an acquisition unit configured to acquire a first signal indicating that the exposure switch is pressed, a first connection unit configured to detachably connect with a control unit of a radiant ray detector to transmit a second signal indicating the driving state of the radiant ray detector, a second connection unit configured to detachably connect with a control unit of a radiant ray generation apparatus to transmit a specific signal, and a control unit configured to perform control to output the specific signal via the second connection unit upon acquisition of the first and second signals, wherein the second connection unit is a connector for making wired connection.

11 Claims, 27 Drawing Sheets

(30) Foreign Application Priority Data

| Apr. 19, 2012 | (JP) | 2012-096096 |
|---|---|---|
| Apr. 19, 2012 | (JP) | 2012-096097 |
| Apr. 19, 2012 | (JP) | 2012-096098 |

(51) Int. Cl.

| H05G 1/56 | (2006.01) |
|---|---|
| H05G 1/32 | (2006.01) |
| H05G 1/34 | (2006.01) |
| H05G 1/38 | (2006.01) |
| H05G 1/40 | (2006.01) |
| H05G 1/42 | (2006.01) |
| H05G 1/44 | (2006.01) |
| H05G 1/46 | (2006.01) |

(52) U.S. Cl.
CPC .......... *A61B 6/4233* (2013.01); *A61B 6/4266* (2013.01); *A61B 6/4283* (2013.01); *A61B 6/54* (2013.01); *A61B 6/548* (2013.01); *A61B 6/56* (2013.01); *A61B 6/563* (2013.01); *A61B 6/566* (2013.01); *H05G 1/30* (2013.01); *H05G 1/32* (2013.01); *H05G 1/34* (2013.01); *H05G 1/38* (2013.01); *H05G 1/40* (2013.01); *H05G 1/42* (2013.01); *H05G 1/44* (2013.01); *H05G 1/46* (2013.01); *H05G 1/56* (2013.01); *A61B 6/4405* (2013.01); *A61B 6/4411* (2013.01); *A61B 6/4441* (2013.01); *A61B 6/465* (2013.01)

(58) Field of Classification Search
CPC .......... A61B 6/56; A61B 6/563; A61B 6/566; A61B 6/4405; A61B 6/4208; A61B 6/4266; A61B 6/4283; H05G 1/30; H05G 1/38; H05G 1/40; H05G 1/42; H05G 1/44; H05G 1/56; H05G 1/32; H05G 1/34; H05G 1/46
USPC .................. 378/62, 91, 114, 115
See application file for complete search history.

(56) References Cited

U.S. PATENT DOCUMENTS

| 7,079,189 | B2 * | 7/2006 | Tsujii | G01T 1/2928 250/208.4 |
|---|---|---|---|---|
| 7,382,859 | B2 | 6/2008 | Nokita et al. | |
| 7,503,693 | B2 | 3/2009 | Jahrling | |
| 7,545,914 | B2 * | 6/2009 | Kito | A61B 6/4283 378/207 |
| 7,561,668 | B2 * | 7/2009 | Ohta | G03B 42/04 378/102 |
| 7,593,507 | B2 * | 9/2009 | Ohta | A61B 6/032 378/207 |
| 7,638,773 | B2 * | 12/2009 | Kuwabara | G03B 42/04 250/370.08 |
| 7,655,916 | B2 * | 2/2010 | Ohta | G01T 7/00 250/370.08 |
| 7,659,533 | B2 * | 2/2010 | Endo | A61B 6/4441 250/580 |
| 7,712,959 | B2 * | 5/2010 | Tanabe | H01J 31/49 250/370.08 |
| 7,732,779 | B2 * | 6/2010 | Kito | A61B 6/548 250/370.09 |
| 7,737,427 | B2 | 6/2010 | Kito et al. | |
| 7,740,405 | B2 * | 6/2010 | Ohta | H01J 31/49 378/189 |
| 7,764,765 | B2 * | 7/2010 | Ohta | A61B 6/4233 250/370.09 |
| 7,767,981 | B2 * | 8/2010 | Kuwabara | A61B 6/4216 250/484.4 |
| 7,772,560 | B2 * | 8/2010 | Ohta | A61B 6/00 250/370.09 |
| 7,777,192 | B2 * | 8/2010 | Ohta | A61B 6/00 250/370.09 |
| 7,777,193 | B2 * | 8/2010 | Kito | G01T 7/00 250/370.09 |
| 7,787,594 | B2 * | 8/2010 | Ohta | A61B 6/4233 378/114 |
| 7,807,976 | B2 * | 10/2010 | Ohta | A61B 6/4233 250/370.09 |
| 7,829,859 | B2 * | 11/2010 | Yoshimi | G03B 42/04 250/370.08 |
| 7,834,322 | B2 * | 11/2010 | Yoshimi | A61B 6/4283 250/370.09 |
| 7,844,031 | B2 | 11/2010 | Newman et al. | |
| 7,847,277 | B2 * | 12/2010 | Kito | A61B 6/00 250/580 |
| 7,856,085 | B2 * | 12/2010 | Hayashida | H04L 67/12 378/98 |
| 7,888,649 | B2 * | 2/2011 | Kito | A61B 6/00 250/370.09 |
| 7,894,575 | B2 * | 2/2011 | Tsubota | A61B 6/548 378/96 |
| 7,924,982 | B2 * | 4/2011 | Watanabe | A61B 6/00 378/114 |
| 7,953,207 | B2 * | 5/2011 | Ohta | A61B 6/4233 250/370.09 |
| 7,974,382 | B2 | 7/2011 | Kitano et al. | |
| 7,991,119 | B2 * | 8/2011 | Yoshida | G01T 1/00 378/114 |
| 7,999,234 | B2 * | 8/2011 | Ohta | A61B 6/4283 250/336.1 |
| 8,053,727 | B2 * | 11/2011 | Nishino | G03B 42/04 250/336.1 |
| 8,080,802 | B2 * | 12/2011 | Nishino | A61B 6/4233 250/370.08 |
| 8,107,590 | B2 * | 1/2012 | Nishino | A61B 6/00 250/370.09 |
| 8,113,712 | B2 | 2/2012 | Tanabe et al. | |
| 8,130,909 | B2 | 3/2012 | Nishino et al. | |
| 8,172,461 | B2 * | 5/2012 | Liu | A61B 6/4283 378/114 |
| 8,174,358 | B2 | 5/2012 | Butzine et al. | |
| 8,182,147 | B2 * | 5/2012 | Nishino | A61B 6/00 378/189 |
| 8,198,593 | B2 * | 6/2012 | Kito | G03B 42/04 250/363.02 |
| 8,213,573 | B2 * | 7/2012 | Liu | A61B 6/4283 378/62 |
| 8,229,202 | B2 * | 7/2012 | Kito | A61B 6/00 378/114 |
| 8,243,883 | B2 | 8/2012 | Omernick et al. | |
| 8,295,439 | B2 | 10/2012 | Yonekawa | |
| 8,319,506 | B2 * | 11/2012 | Liu | A61B 6/4283 324/691 |
| 8,325,875 | B2 | 12/2012 | Omernick et al. | |
| 8,330,597 | B2 * | 12/2012 | Nishino | A61B 6/00 250/370.01 |
| 8,331,530 | B2 | 12/2012 | Butzine et al. | |
| 8,334,515 | B2 * | 12/2012 | Tsubota | A61B 6/548 250/370.08 |
| 8,334,516 | B2 * | 12/2012 | Tsubota | A61B 6/4283 250/370.08 |
| 8,357,908 | B2 * | 1/2013 | Kuwabara | A61B 6/56 250/370.08 |
| 8,358,740 | B2 * | 1/2013 | Nakatsugawa | A61B 6/102 378/116 |
| 8,364,241 | B2 * | 1/2013 | Hannon | A61B 6/4494 378/114 |
| 8,396,188 | B2 | 3/2013 | Liu et al. | |
| 8,401,150 | B2 | 3/2013 | Watanabe | |
| 8,421,024 | B2 * | 4/2013 | Ohta | G03B 42/02 250/370.08 |
| 8,523,433 | B2 | 9/2013 | Butzine et al. | |
| 8,552,392 | B2 * | 10/2013 | Kito | G03B 42/04 250/370.09 |
| 8,618,494 | B2 * | 12/2013 | Konishi | H04N 5/32 250/394 |

(56) References Cited

U.S. PATENT DOCUMENTS

| | | | | |
|---|---|---|---|---|
| 8,675,624 B2* | 3/2014 | Tachikawa | A61B 6/4494 | 370/338 |
| 8,781,073 B2* | 7/2014 | Kim | A61B 6/46 | 378/98 |
| 8,824,634 B2* | 9/2014 | Lalena | A61B 6/08 | 378/108 |
| 8,855,691 B2 | 10/2014 | Kamiya et al. | | |
| 8,873,712 B2* | 10/2014 | Wang | A61B 6/08 | 378/97 |
| 8,879,689 B2* | 11/2014 | Ohta | A61B 6/4233 | 378/108 |
| 8,899,831 B2* | 12/2014 | Yoshida | A61B 6/4233 | 250/370.08 |
| 8,903,048 B2 | 12/2014 | Kitano et al. | | |
| 8,923,482 B2 | 12/2014 | Tajima | | |
| 8,953,742 B2* | 2/2015 | Yoshida | A61B 6/4233 | 378/114 |
| 8,953,744 B2* | 2/2015 | Watanabe | H04N 5/32 | 250/370.09 |
| 8,956,045 B2* | 2/2015 | Tajima | A61B 6/4283 | 378/145 |
| 8,970,755 B2* | 3/2015 | Nishino | H04N 5/32 | 250/370.09 |
| 8,971,494 B2 | 3/2015 | Tajima | | |
| 8,983,035 B2* | 3/2015 | Noma | H05G 1/64 | 250/214 DC |
| 9,001,972 B2* | 4/2015 | Takahashi | H05G 1/30 | 378/62 |
| 9,041,351 B2* | 5/2015 | Ikegame | H02J 7/0045 | 320/107 |
| 9,042,519 B2 | 5/2015 | Kuwabara et al. | | |
| 9,046,609 B2* | 6/2015 | Chicchetti | G01T 7/00 | |
| 9,050,051 B2* | 6/2015 | Nakatsugawa | A61B 6/4233 | |
| 9,050,059 B2 | 6/2015 | Kuwabara | | |
| 9,055,922 B2 | 6/2015 | Kuwabara et al. | | |
| 9,060,731 B2* | 6/2015 | Kuwabara | A61B 6/4233 | |
| 9,060,738 B2* | 6/2015 | Kuwabara | A61B 6/548 | |
| 9,078,624 B2 | 7/2015 | Sugizaki | | |
| 9,097,643 B2* | 8/2015 | Tsuchiya | A61B 6/4233 | |
| 9,101,316 B2* | 8/2015 | Liu | A61B 6/4233 | |
| 9,101,325 B2* | 8/2015 | Wang | A61B 6/545 | |
| 9,101,328 B2 | 8/2015 | Tsuji | | |
| 9,119,584 B2* | 9/2015 | Sato | H04N 5/32 | |
| 9,146,326 B2 | 9/2015 | Kuwabara et al. | | |
| 9,168,011 B2* | 10/2015 | Nenoki | A61B 6/4283 | |
| 9,192,350 B2* | 11/2015 | Hiroike | H05G 1/08 | |
| 9,198,271 B2* | 11/2015 | Miyachi | H05G 1/30 | |
| 9,232,620 B2* | 1/2016 | Tajima | H05G 1/42 | |
| 9,258,497 B2* | 2/2016 | Tsuji | H04N 5/32 | |
| 9,259,201 B2* | 2/2016 | Sato | A61B 6/4233 | |
| 9,265,467 B2* | 2/2016 | Kamiya | A61B 6/5241 | |
| 9,268,041 B2* | 2/2016 | Ohta | G01T 1/2018 | |
| 9,320,482 B2* | 4/2016 | Tajima | A61B 6/42 | |
| 9,322,928 B2* | 4/2016 | Iwakiri | A61B 6/4233 | |
| 9,351,699 B2* | 5/2016 | Kuwabara | A61B 6/542 | |
| 9,439,611 B2* | 9/2016 | Peterson | A61B 6/40 | |
| 9,462,990 B2* | 10/2016 | Kuwabara | A61B 6/54 | |
| 9,521,987 B2* | 12/2016 | Tajima | A61B 6/08 | |
| 9,579,076 B2* | 2/2017 | Tajima | H05G 1/44 | |
| 9,629,591 B2* | 4/2017 | Liu | A61B 6/4283 | |
| 9,629,601 B2* | 4/2017 | Tajima | A61B 6/4208 | |
| 9,668,331 B2* | 5/2017 | Takahashi | H04N 5/32 | |
| 9,750,477 B2* | 9/2017 | Kitagawa | A61B 6/542 | |
| 9,753,158 B2* | 9/2017 | Nishino | A61B 6/582 | |
| 10,074,679 B2* | 9/2018 | Tajima | A61B 6/4233 | |
| 10,076,291 B2* | 9/2018 | Arai | A61B 6/06 | |
| 2002/0102974 A1 | 8/2002 | Raith | | |
| 2007/0280420 A1 | 12/2007 | Jahrling | | |
| 2009/0032744 A1 | 2/2009 | Kito et al. | | |

FOREIGN PATENT DOCUMENTS

| | | |
|---|---|---|
| CN | 101868181 A | 10/2010 |
| JP | 392400 A | 4/1991 |
| JP | 11155847 A | 6/1999 |
| JP | 11244273 A | 9/1999 |
| JP | 2000308632 A | 11/2000 |
| JP | 2004141473 A | 5/2004 |
| JP | 2006247102 A | 9/2006 |
| JP | 2006247137 A | 9/2006 |
| JP | 2006263322 A | 10/2006 |
| JP | 2008-029393 A | 2/2008 |
| JP | 2008237445 A | 10/2008 |
| JP | 2009034428 A | 2/2009 |
| JP | 2010-075663 A | 4/2010 |
| JP | 2010-223863 A | 10/2010 |
| JP | 2010-262134 A | 11/2010 |
| JP | 2010-264000 A | 11/2010 |
| JP | 2011072358 A | 4/2011 |
| JP | 2011104083 A | 6/2011 |
| JP | 2011120885 A | 6/2011 |
| JP | 2012070886 A | 4/2012 |
| JP | 2012139258 A | 7/2012 |
| WO | 2006/101233 A1 | 9/2006 |
| WO | 10/073838 A1 | 7/2010 |

* cited by examiner

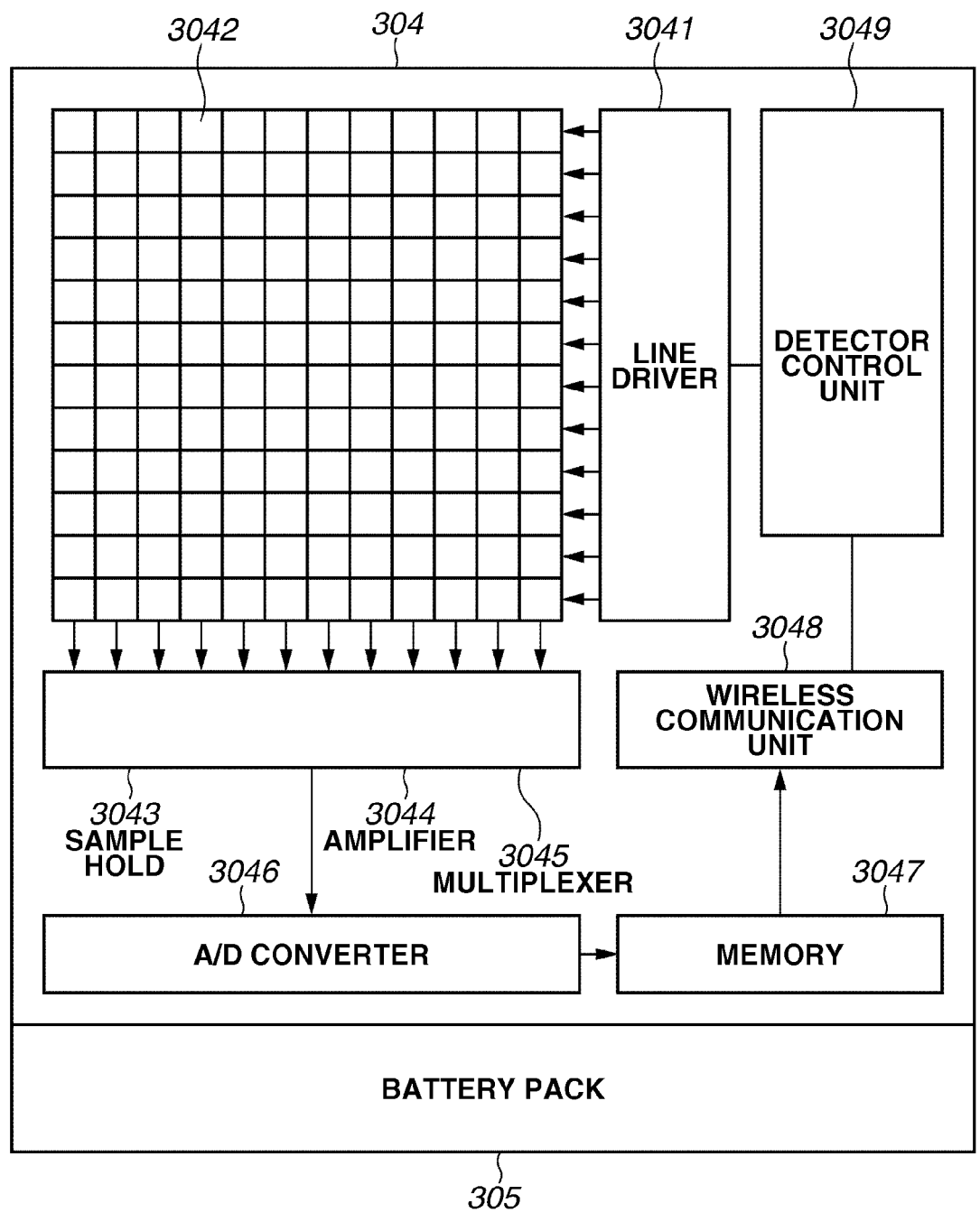

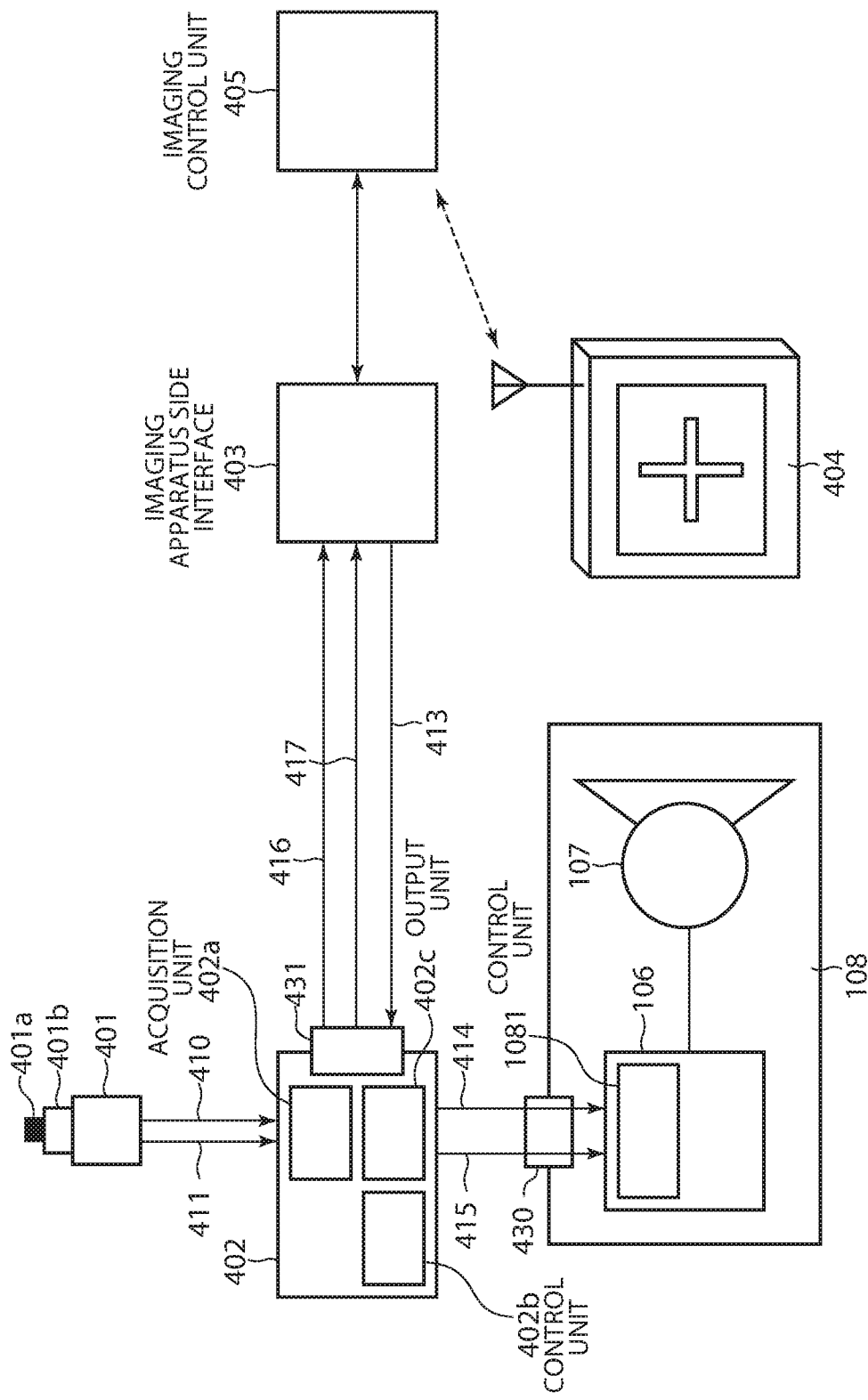

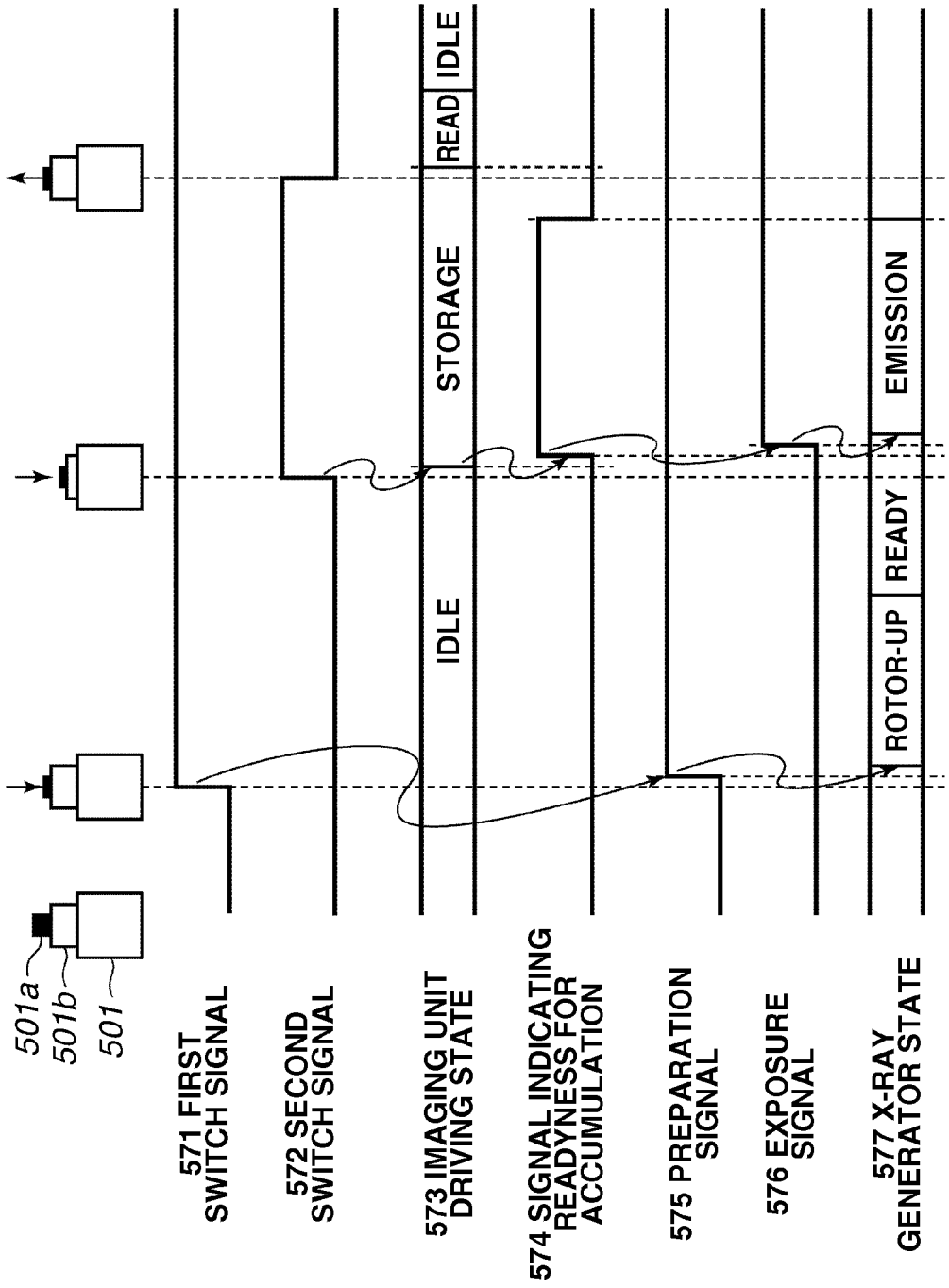

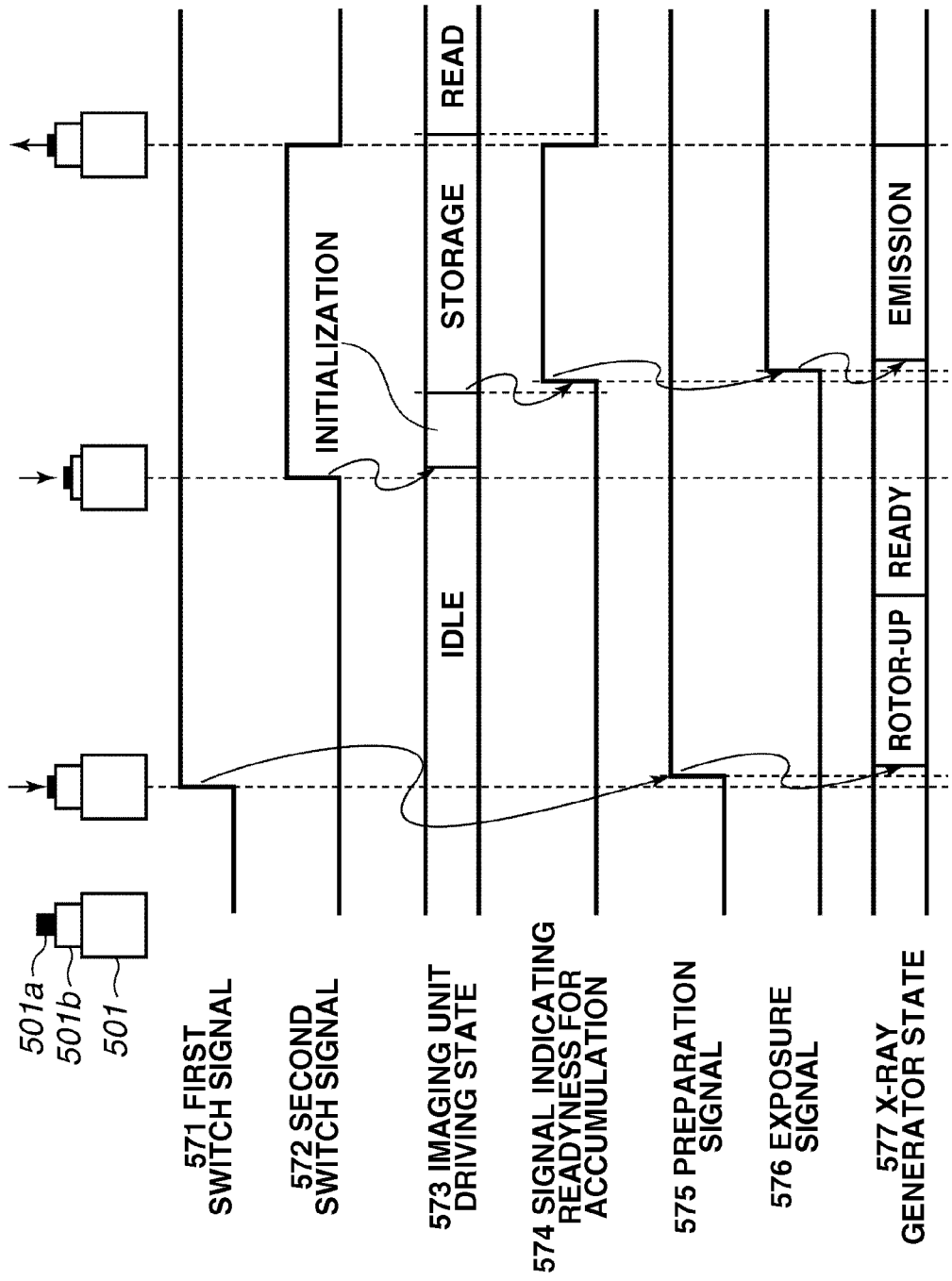

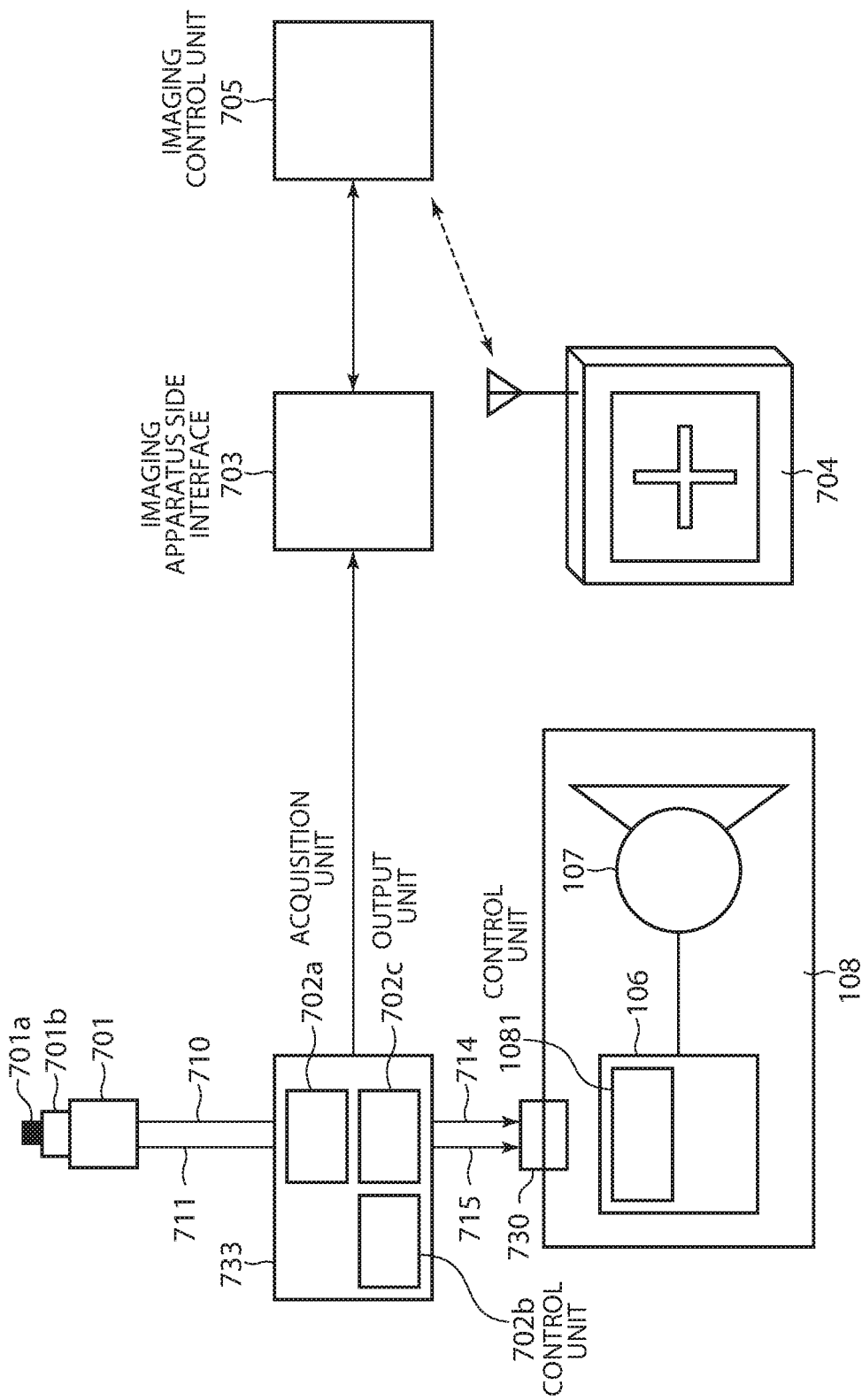

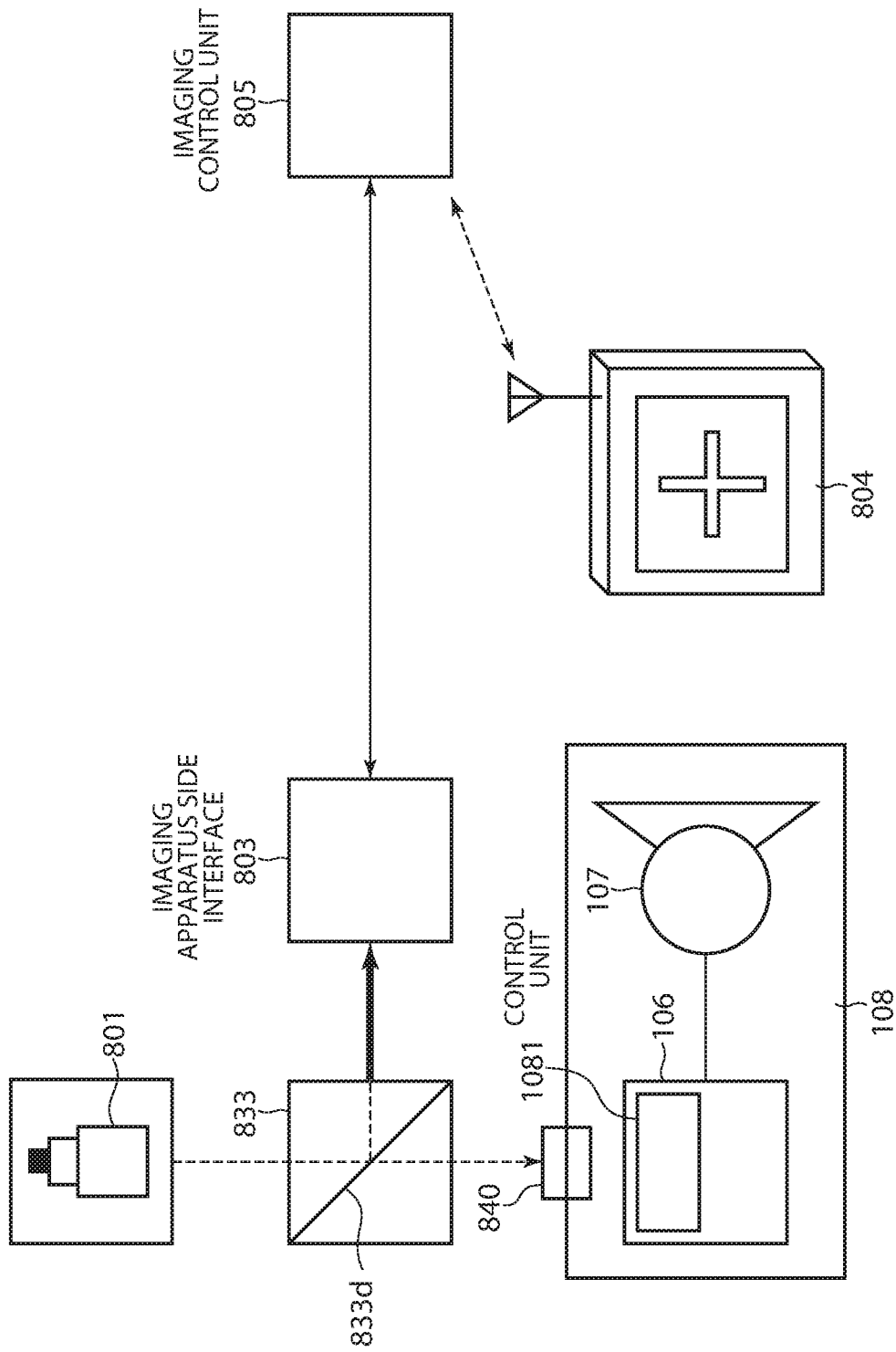

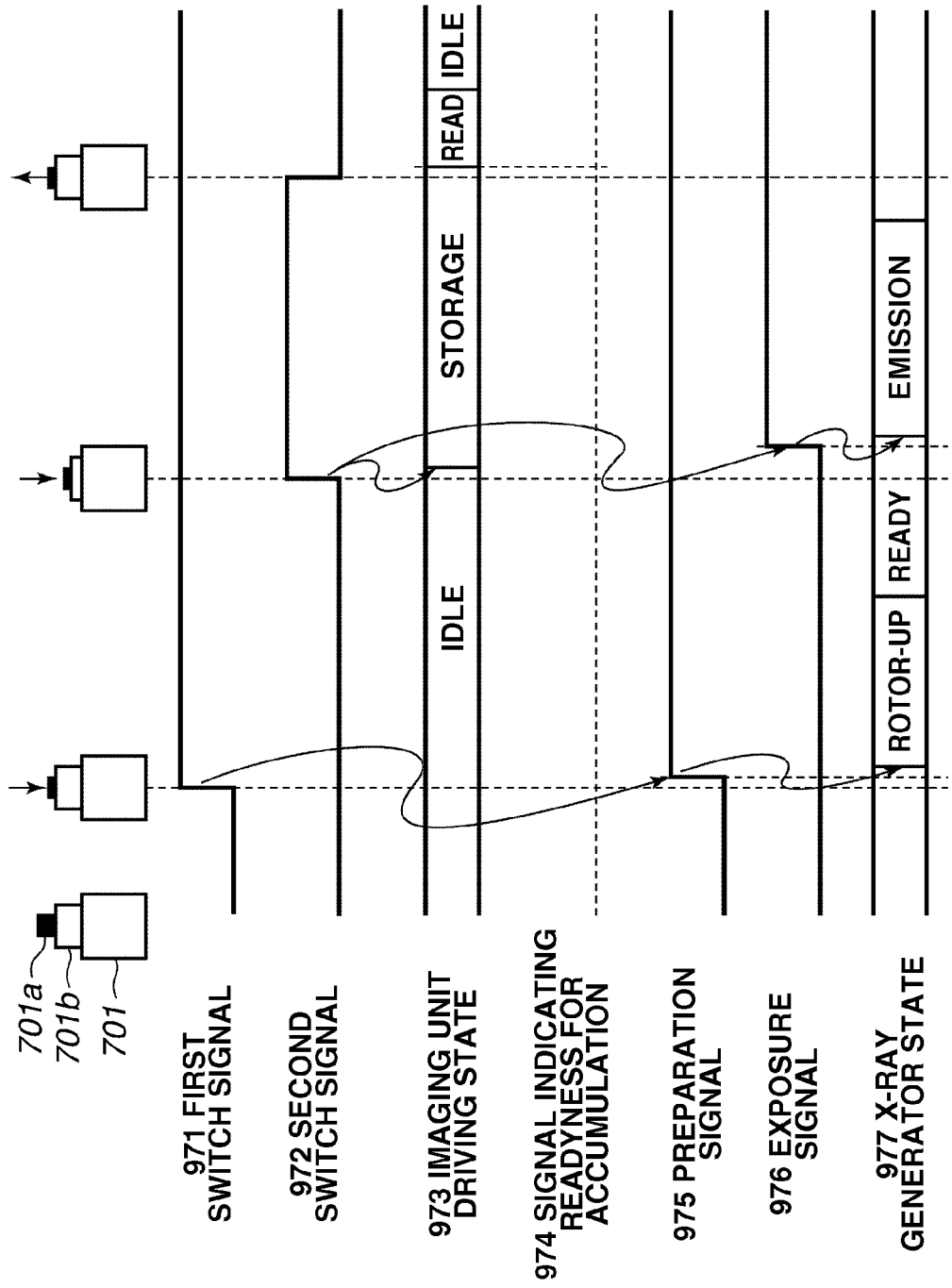

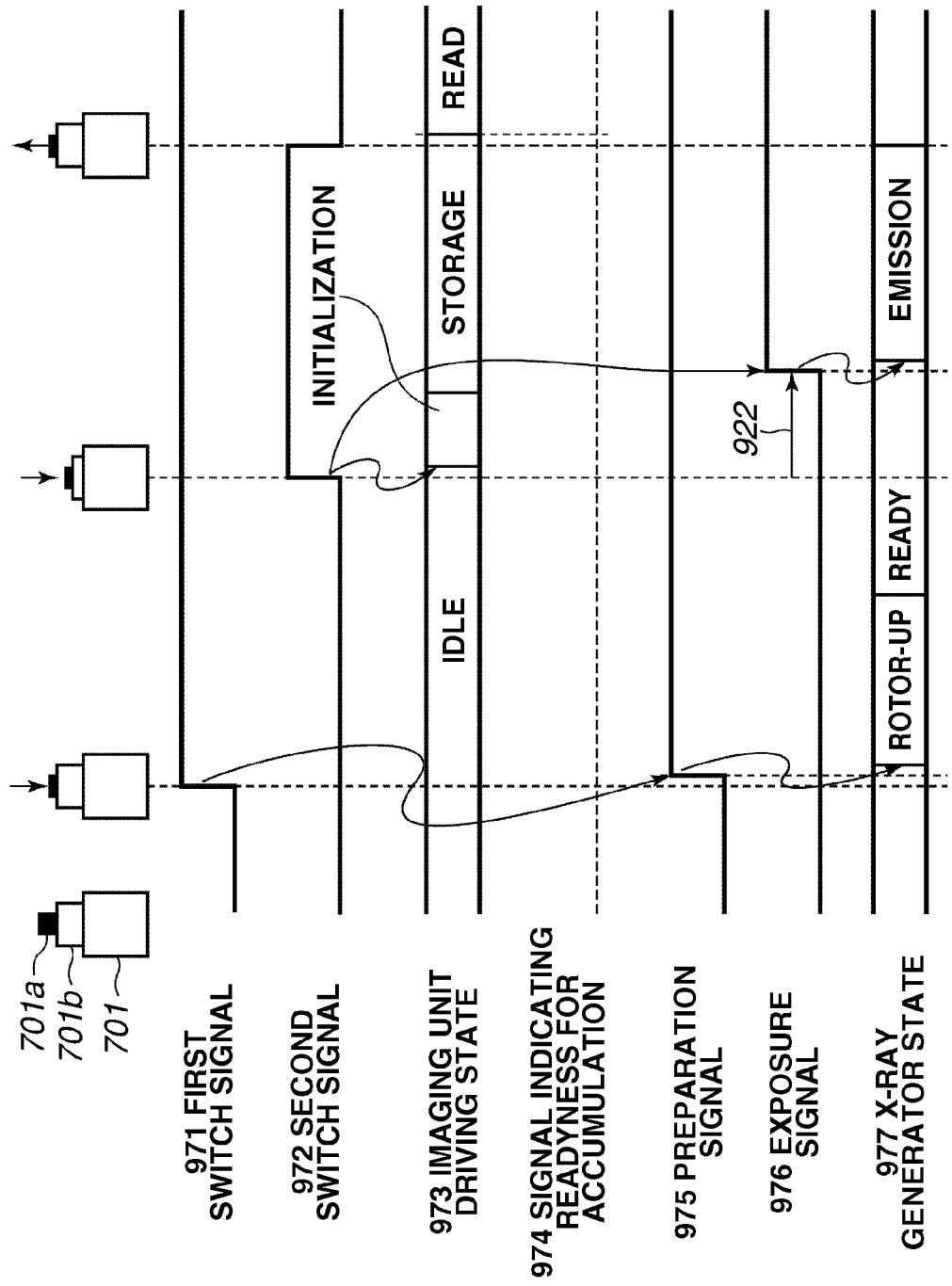

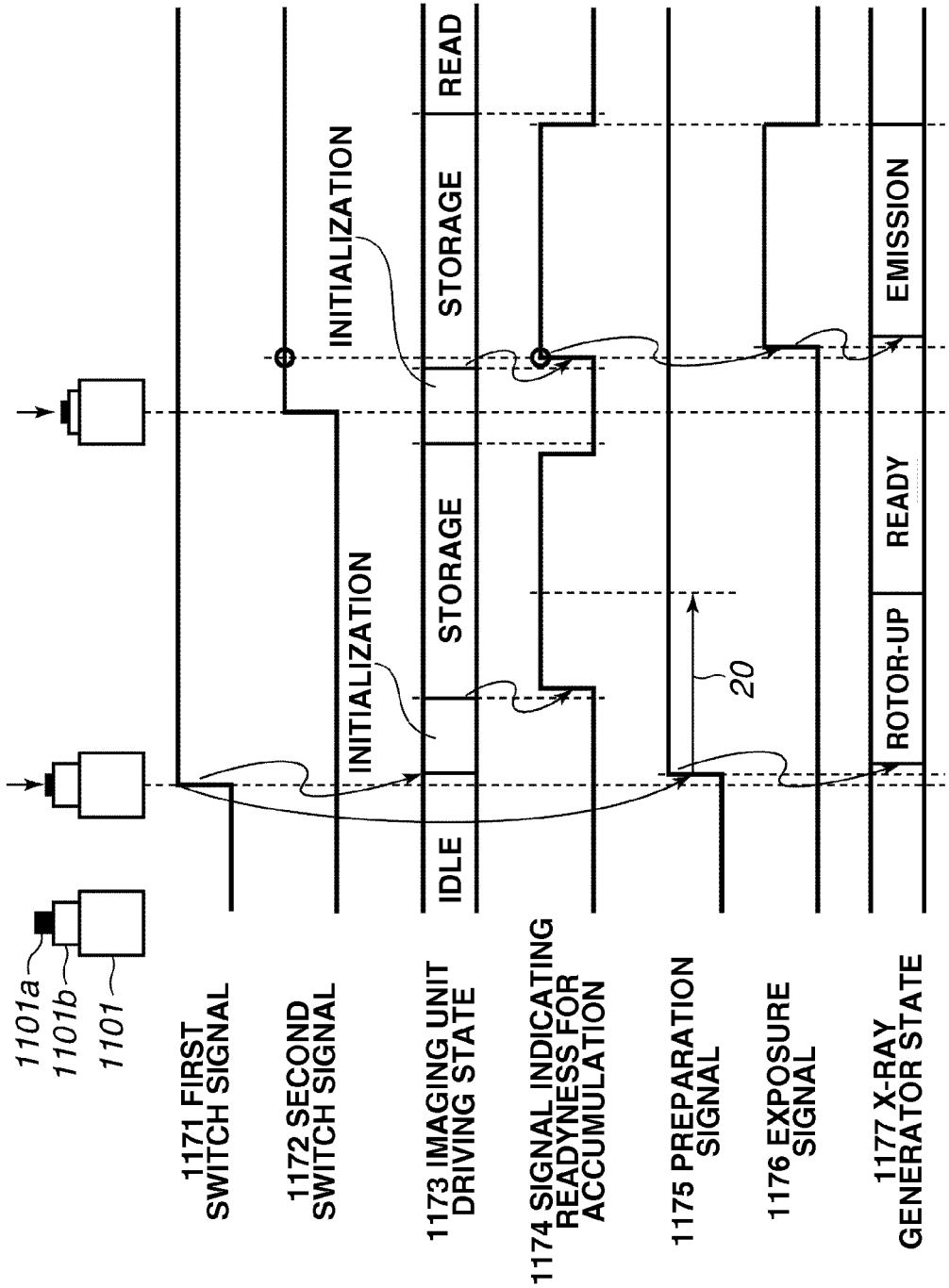

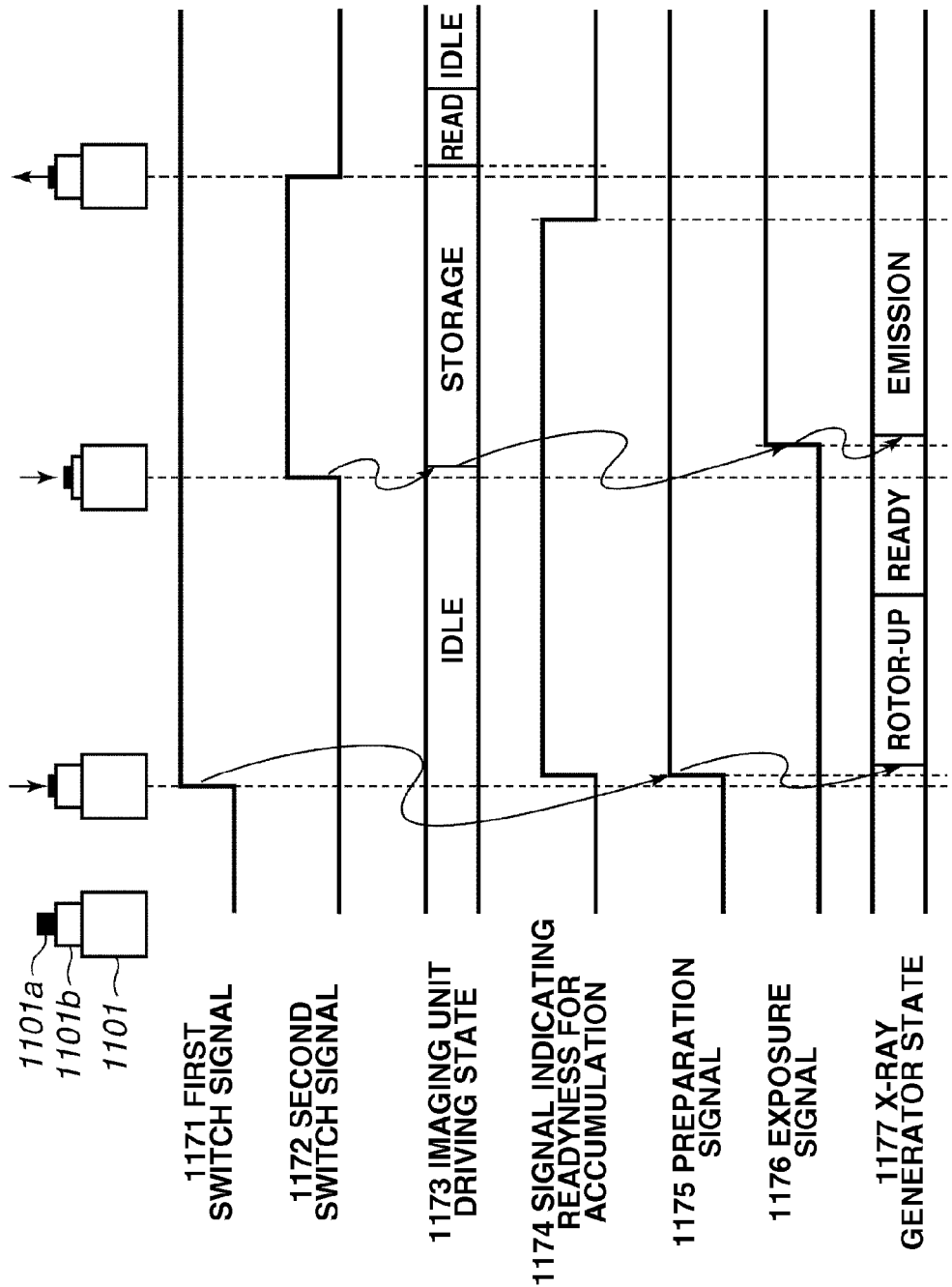

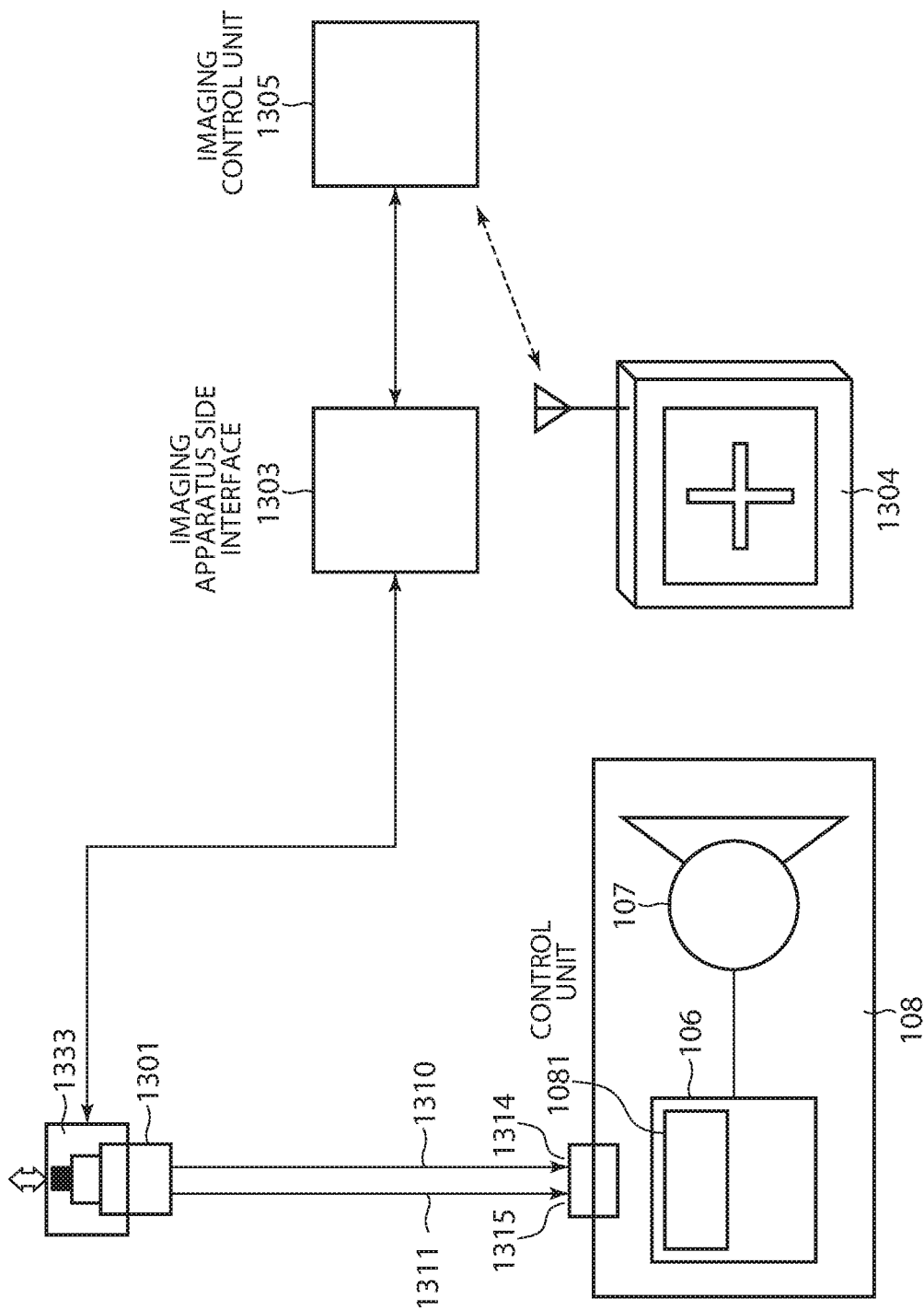

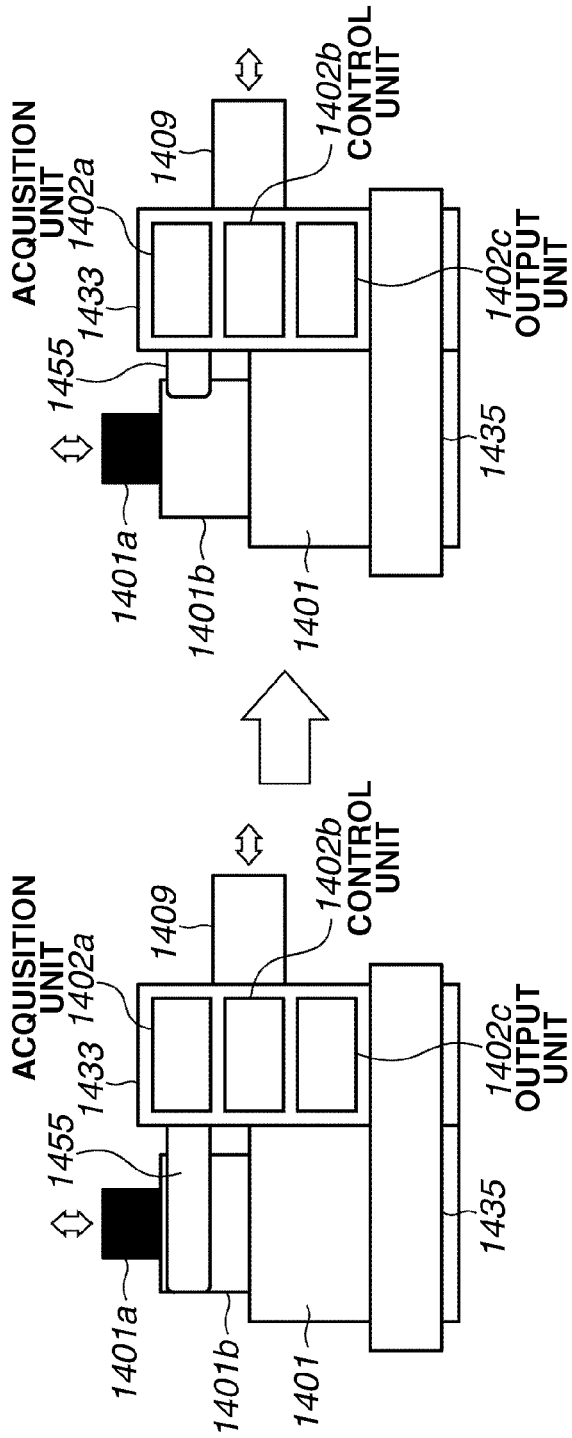

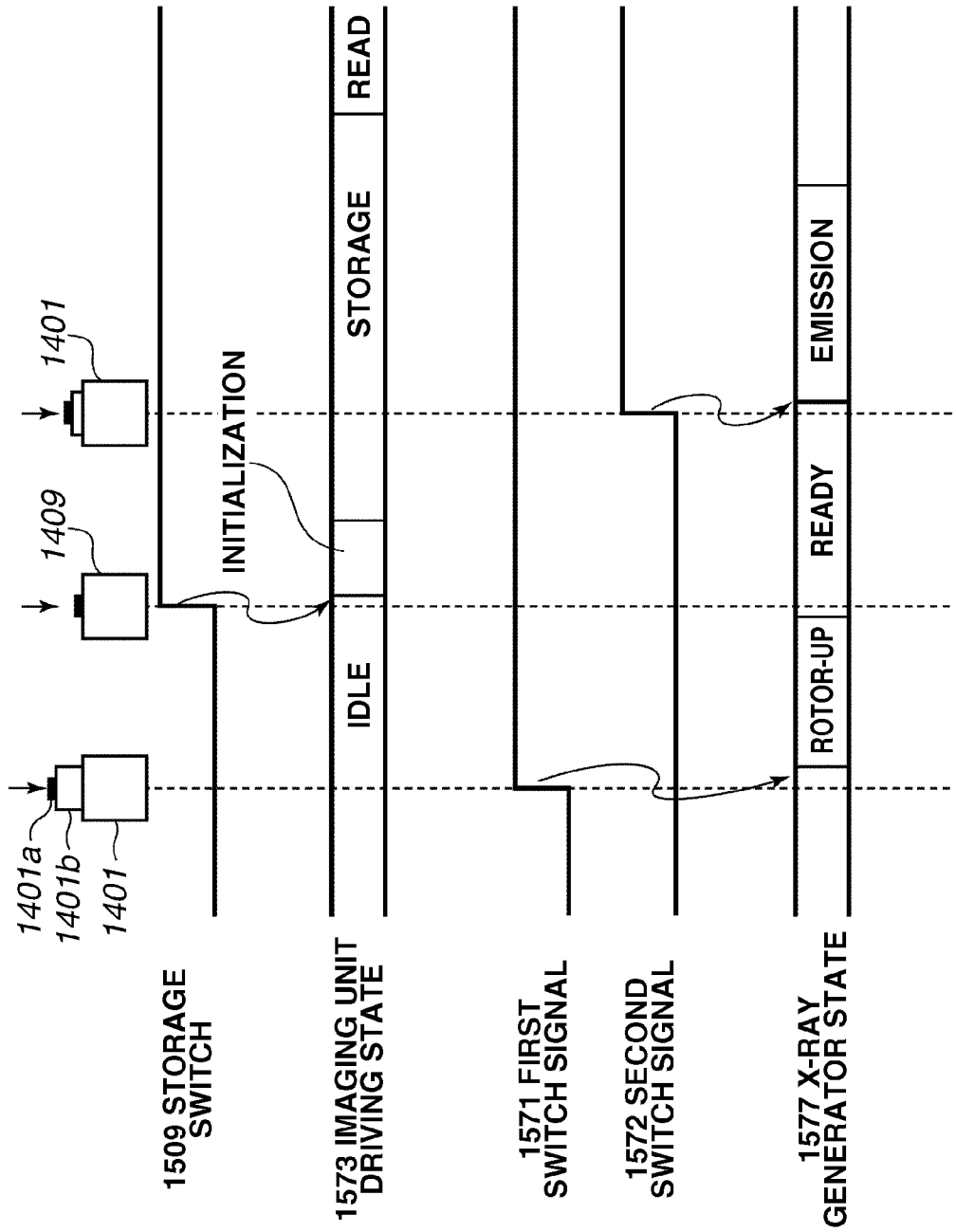

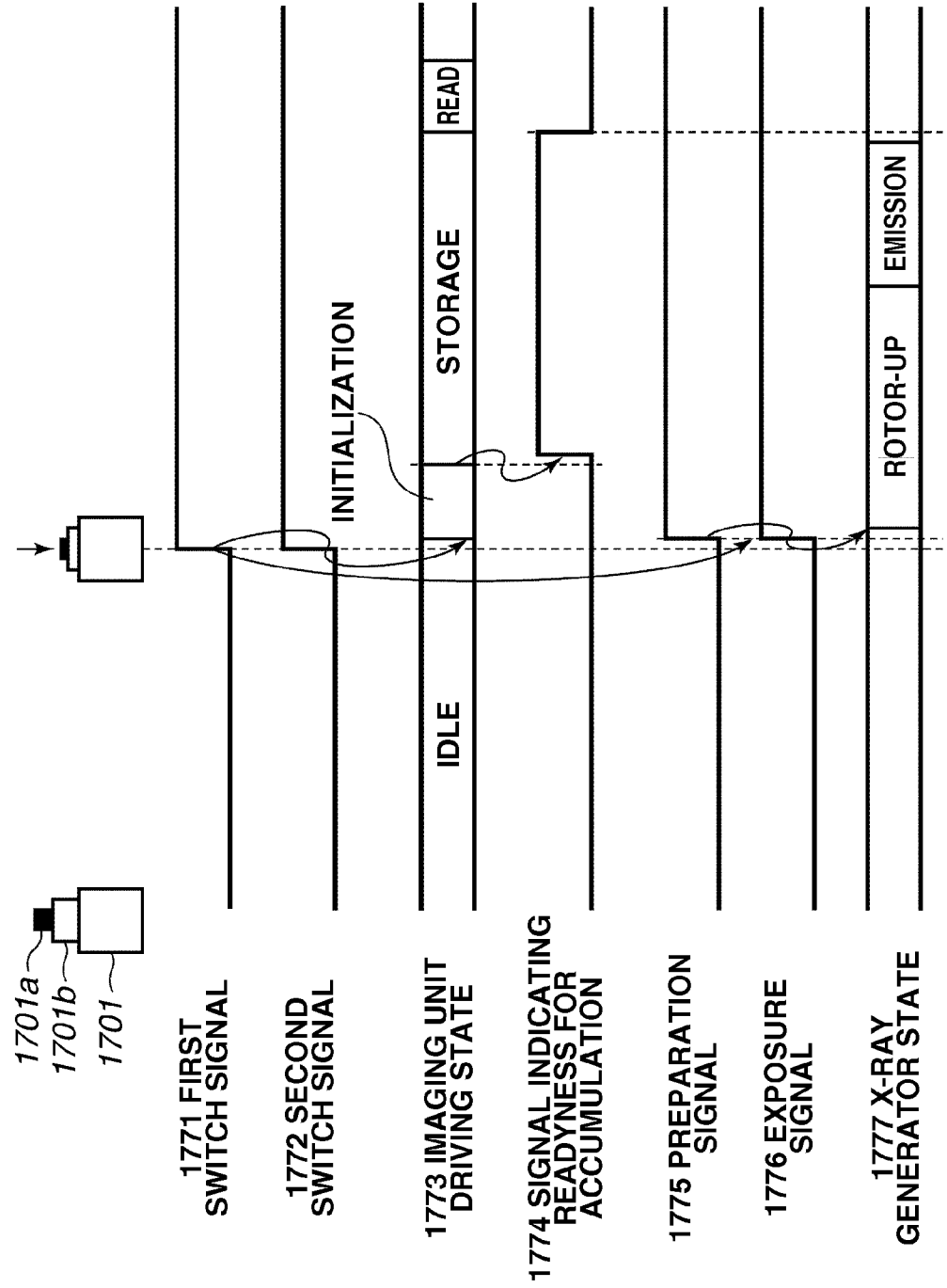

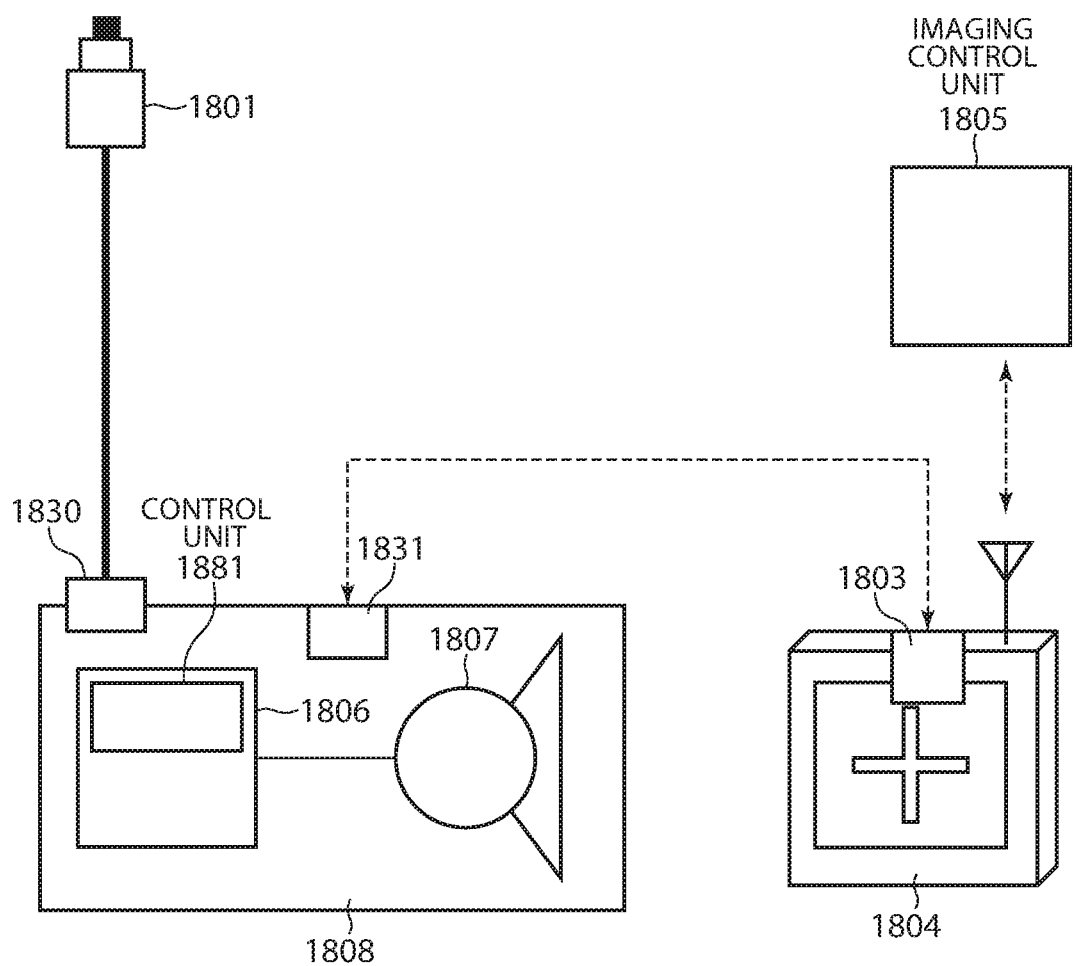

RADIANT RAY GENERATION CONTROL APPARATUS, RADIATION IMAGING SYSTEM, AND METHOD FOR CONTROLLING THE SAME

CROSS-REFERENCE TO RELATED APPLICATIONS

This application is a Continuation of co-pending U.S. patent application Ser. No. 13/865,618 filed Apr. 18, 2013, which claims foreign priority benefit of Japanese Patent Applications No. 2012-096094 filed Apr. 19, 2012; No. 2012-096095 filed Apr. 19, 2012; No. 2012-096096 filed Apr. 19, 2012; No. 2012-096097 filed Apr. 19, 2012; and No. 2012-096098 filed Apr. 19, 2012. The disclosures of the above-named applications are hereby incorporated by reference herein in their entirety.

BACKGROUND OF THE INVENTION

Field of the Invention

The present invention relates to a radiant ray generation control apparatus, a radiation imaging system, and a method for controlling the same.

Description of the Related Art

A digital X-ray imaging system including an X-ray generator for irradiating an object with X-ray, and an X-ray detector for acquiring as digital data an X-ray image representing the intensity distribution of X-ray which penetrated the object has been commercially manufactured.

Such a digital X-ray imaging system performs X-ray imaging while controlling the state of the X-ray detector, such as activation of the X-ray detector and transition to a storage state. Japanese Patent Application Laid-Open No. 2000-308632 discusses a technique for controlling the state of an X-ray detector by transmitting information about an X-ray exposure switch from an X-ray generator to the X-ray detector, thus performing imaging control. Further, Japanese Patent Application Laid-Open No. 11-155847 discusses a technique for changing, when an X-ray detector detects X-ray generated by an X-ray generator, the X-ray detector to a state where X-ray can be detected to acquire an X-ray image.

However, signal exchange between the X-ray generator and the X-ray detector as discussed in Japanese Patent Application Laid-Open No. 2000-308632 becomes difficult if the X-ray generator is not provided with a dedicated interface. When the X-ray detector performs state transition upon detection of X-ray as discussed in Japanese Patent Application Laid-Open No. 11-155847, delayed detection of the activation and deactivation of X-ray emission will cause degradation in image quality.

SUMMARY OF THE INVENTION

A radiation imaging control apparatus includes an exposure switch configured to instruct radiation emission, an acquisition unit configured to acquire a first signal indicating that the exposure switch is pressed, a first connection unit configured to detachably connect with a control unit of a radiant ray detector to transmit a second signal indicating the driving state of the radiant ray detector, a second connection unit configured to detachably connect with a control unit of a radiant ray generation apparatus to transmit a specific signal, and a control unit configured to perform control to output the specific signal via the second connection unit upon acquisition of the first and second signals, wherein the second connection unit is a connector for making wired connection.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

FIG. 3 illustrates an internal configuration of an X-ray detector.

FIG. 4 illustrates examples of signals exchanged in an X-ray imaging system.

FIG. 5A is a timing chart illustrating signal states at the start of imaging.

FIG. 5B is a timing chart when an X-ray detector according to another exemplary embodiment is used.

FIG. 7 is a block diagram illustrating an X-ray imaging system including a switching unit having a synchronization interface performing unidirectional communication according to an exemplary embodiment.

FIG. 8 is a block diagram illustrating an X-ray imaging system including a switching unit having a synchronization interface performing unidirectional communication according to still another exemplary embodiment.

FIG. 9A is a timing chart illustrating signal states at the start of imaging when a synchronization interface performing unidirectional communication is used.

FIG. 9B is a timing chart when an X-ray detector according to still another exemplary embodiment is used.

FIG. 11A is a timing chart illustrating signal states according to an exemplary embodiment.

FIG. 11B is a timing chart when an X-ray detector according to still another exemplary embodiment is used.

FIG. 13 illustrates a configuration of an X-ray imaging system when an exposure switch is provided with a synchronization interface.

FIG. 14 illustrates an example configuration of a synchronization interface provided on the exposure switch.

FIG. 15A is a timing chart when a synchronization interface is provided on the exposure switch.

FIG. 17A is a timing chart illustrating control according to an exemplary embodiment.

FIG. 18B is a block diagram illustrating an X-ray imaging system for directly communicating with an X-ray generator and an X-ray detector via the command communication interface.

DESCRIPTION OF THE EMBODIMENTS

Figure 1:
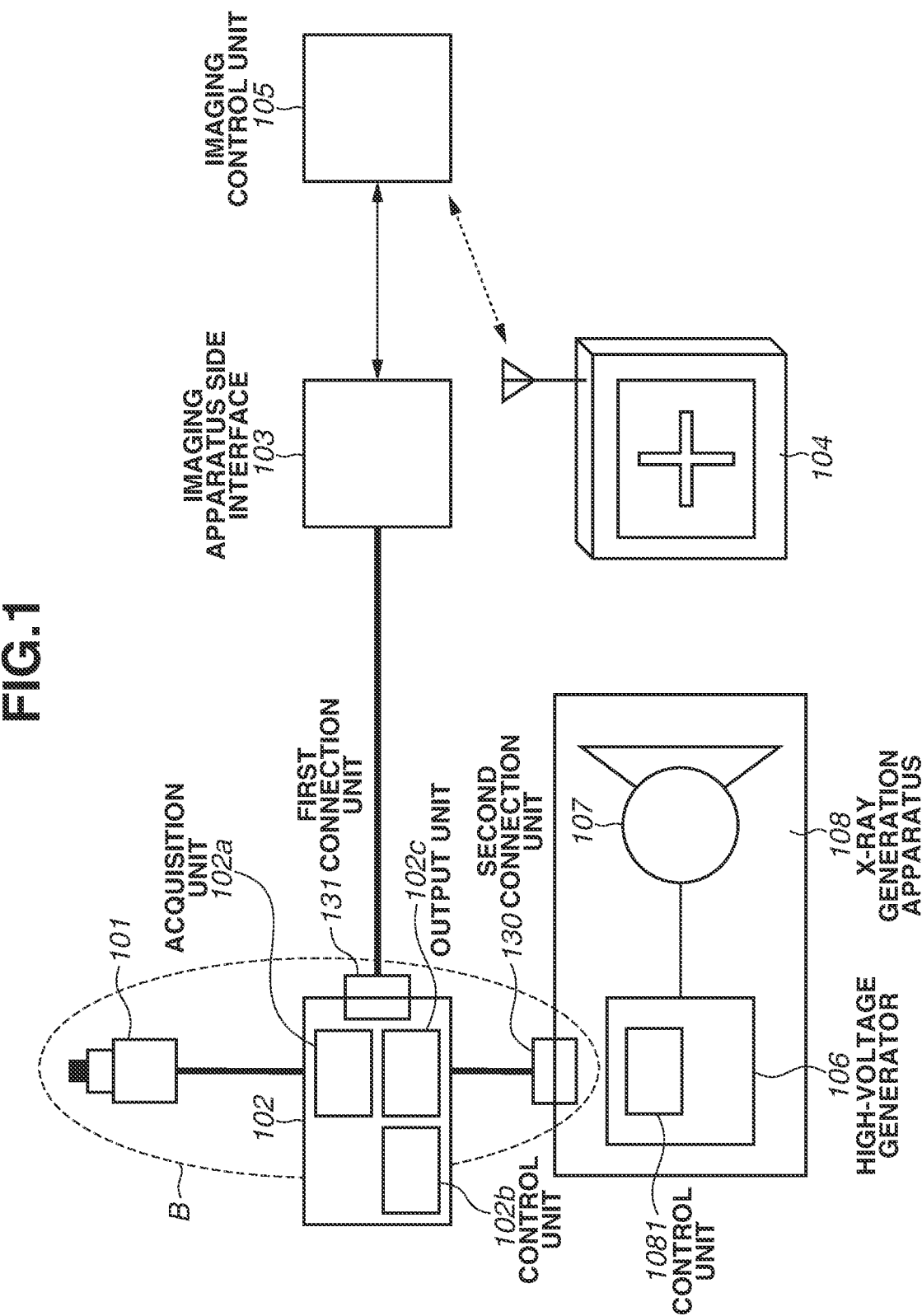
FIG. 1 is a block diagram illustrating an X-ray imaging system when a switching unit having a synchronization interface is connected to an X-ray generator.

Various exemplary embodiments, features, and aspects of the invention will be described in detail below with reference to the drawings.

The following describes a radiation imaging system according an exemplary embodiment of the present invention. Examples of radiation systems include mobile visiting cars, mobile C-arms, and stationary X-ray imaging systems. In the descriptions of the following exemplary embodiments, units having the same function or element are assigned reference numerals having identical two lowest digits.

The following describes a radiation imaging system according to an exemplary embodiment, with reference to FIG. 1. The radiation imaging system includes a radiant ray detector 104 for detecting radiant ray, such as X-ray, to acquire a digital radiographic image, and a radiant ray generation apparatus 108 for emitting radiant ray, such as X-ray. The radiant ray detector 104 and the radiant ray generation apparatus 108 can exchange signals via a radiant ray generation control apparatus B. In the descriptions of the following exemplary embodiments, the radiant ray generation apparatus 108 is sometimes referred to as a radiation imaging control apparatus since it performs imaging control. Further, the radiant ray generation control apparatus B is sometimes referred to as a switching unit B since it includes an exposure switch 101.

The radiant ray detector 104 detects radiation ray to acquire a digital radiographic image. The radiant ray detector 104 communicates with the radiant ray generation apparatus B via an imaging apparatus side interface (I/F) 103, and the imaging control unit 105 for controlling the radiant ray detector 104. The imaging apparatus side I/F 103, the imaging control unit 105, and the radiant ray detector 104 are sometimes collectively referred to as an imaging apparatus or a radiation imaging apparatus. There is a case where the imaging apparatus side I/F 103 connects with the radiant ray detector 104 directly or via an access point in a local area network (LAN) configuration.

The radiant ray generation apparatus 108 includes a high-voltage generator 106 including a control unit 1081, and a radiation source 107 including an X-ray tube.

The radiant ray generation control apparatus B is an exposure switch unit which includes the exposure switch 101, a generation apparatus side I/F 102, an imaging apparatus side connection unit 131 (first connection unit), and a generation apparatus side connection unit 130 (second connection unit). The exposure switch 101 is used to instruct radiation emission. When pressed by a photographer, such as a technician and doctor, the exposure switch 101 generates and outputs a signal (first signal) indicating that the exposure switch 101 is pressed. When the radiant ray generation apparatus 108 receives the first signal, the radiant ray generation apparatus 108 performs radiation emission preparation and radiation emission instruction. The exposure switch 101 includes a detector for electromagnetically, mechanically, or optically detecting the depression, and an output unit for outputting, upon detection of the depression, an electrical or optical signal (first signal) via a conduction cable.

The generation apparatus side I/F 102 includes an acquisition unit 102a, a control unit 102b, and an output unit 102c, and is connected by cable to the exposure switch 101. The generation apparatus side I/F 102 is detachably connected with the imaging control unit 105 on the imaging apparatus side (on the side of the radiant ray detector 104) via the imaging apparatus side connection unit 131. The generation apparatus side I/F 102 is further detachably connected with the control unit 1081 of the radiant ray generation apparatus 108 via the generation apparatus side connection unit 130.

The imaging apparatus side connection unit 131 is configured, for example, of a connector for connecting by cable with a connection unit on the side of the imaging apparatus side I/F 103.

The generation apparatus side connection unit 130 is configured, for example, of a connector detachably connectable with a connection unit of the radiant ray generation apparatus 108.

The acquisition unit 102a is electrically connected with the exposure switch 101 to receive the first signal indicating that the exposure switch 101 is pressed. The acquisition unit 102a further acquires a signal that has reached the generation apparatus side I/F 102 via the imaging apparatus side connection unit 131 and the generation apparatus side connection unit 130.

The radiant ray detector 104 outputs a signal (second signal) indicating the driving state of the radiant ray detector 104. Although an output signal may be transmitted by cable, a wireless transmission unit for wireless transmission may be provided in the radiant ray detector 104. This enables imaging by using the radiant ray detector 104 without being bothered by cables.

The radiant ray detector 104 outputs a signal indicating that the radiant ray detector 104 has received radiant ray and shifted to the imaging ready state. The radiant ray detector 104 constantly or periodically outputs a signal (second signal) indicating the driving state of the radiant ray detector 104 to the radiant ray generation control apparatus B.

The imaging control unit 105 of the radiant ray detector 104 and the imaging apparatus side I/F 103 transmit the output second signal to the imaging apparatus side connection unit 131, and the acquisition unit 102a acquires the second signal.

When the acquisition unit 102a acquires the first signal from the exposure switch 101 and the second signal from the radiant ray detector 104, the control unit 102b performs control to output a specific signal via the generation apparatus side connection unit 130 (second connection unit).

Although the specific signal may be any one of the first signal, the second signal, and a third signal different therefrom, transmitting both the first and second signals improves reliability.

When the exposure switch 101 outputs the first signal as the specific signal upon reception of the second signal, the radiant ray generation apparatus 108 preferably receives and interprets the signal of the exposure switch 101 as usual. Therefore, even with the radiant ray generation apparatus 108 used for analog radiation imaging, the switching unit B having a detachably attachable switch enables digital radiation imaging.

By connecting a connection unit on the side of the radiant ray generation apparatus 108 with the generation apparatus side connection unit 130, the switching unit B is connected with the control unit 1081 of the radiant ray generation apparatus 108. Thus, the radiant ray generation apparatus 108 receives the specific signal from the switching unit B. Upon reception of the relevant specific signal, the control unit 1081 controls the high-voltage generator 106 to generate a high voltage for radiant ray generation, and also controls the radiation source 107 to generate radiant ray.

The radiant ray detector 104 detects the generated radiant ray to acquire radiographic image data. For example, a wireless transmission unit transmits the radiographic image data to the imaging control unit 105. The imaging control unit 105 including a display control unit can display on a display unit the radiographic image output by the radiant ray detector 104.

As described above, the radiant ray generation control apparatus B is detachably connected with the imaging apparatus including the radiant ray detector 104 and the radiant ray generation apparatus 108 to communicate with them upon depression of the exposure switch 101. Connecting a detachably connectable connection unit of the switching unit B to the radiant ray generation apparatus 108 enables signal exchange between the radiant ray generation apparatus 108 and the radiant ray detector 104. Thus, it becomes possible to easily build a system capable of digital radiation imaging, such as pre-imaging imaging condition exchange, synchronization at the time of imaging, imaging operation information exchange, and image transmission.

In another exemplary embodiment, when the acquisition unit 102a receives the signal from the exposure switch 101, the control unit 102b performs control to output via the imaging apparatus side connection unit 131 a third signal for requesting information about the driving state of the radiant ray detector 104. As the third signal, the first signal can be output as it is to the imaging apparatus side. In response to the third signal, the radiant ray detector 104 outputs a signal (second signal) indicating the driving state of the radiant ray detector 104. The radiant ray detector 104 changes the driving state from the wait state to the imaging ready state, for example, in response to the third signal. Further, upon depression of the exposure switch 101, the radiant ray detector 104 outputs a signal indicating that it has received radiant ray and shifted to the imaging ready state.

Thus, since the radiant ray detector 104 can perform a state transition upon depression of the exposure switch 101, the radiant ray detector 104 does not need to be retained in the wait state for a prolonged time period, reducing degradation of the radiant ray detector 104.

Further, in this case, if the generation apparatus side I/F 102 is disposed as a circuit in the housing of the exposure switch 101, it becomes unnecessary to dispose the switching unit B between the exposure switch 101 and the connection unit 130, making it easier to handle the switching unit B. In this case, the switching unit B includes the acquisition unit 102a for acquiring the signal (first signal) indicating that the exposure switch 101 is pressed, the connection unit 131 for connecting with the radiant ray detector 104, and the control unit 102b for outputting the specific signal to the radiant ray generation apparatus 108 via the connection unit 130 in response to the first signal and the second signal from the radiant ray detector 104.

In addition, by providing in the housing of the exposure switch 101 a display unit for displaying the progress of imaging, and a display control unit for controlling the display unit to display the acquisition of the second signal, the photographer holding the exposure switch 101 can easily confirm the communication state from his or her viewpoint.

Although the switching unit B may communicate with the imaging apparatus via a wire cable as illustrated in the FIG. 1, wirelessly communicating with the imaging apparatus side I/F 103 reduces the possibility of being bothered by cables. In this case, the connection unit 131 serves as a communication unit for performing wireless signal transmission and reception. Conversely, in a case where a modality, such as a visiting car and C arm, is provided with the imaging apparatus side I/F 103, for example, the reliability can be improved by connecting the imaging apparatus side I/F 103 with the switching unit B with a wire cable.

Communication between the switching unit B and the imaging apparatus may use a dedicated communication line handling the voltage value as it is as a signal. However, command communication in which data 0 and 1 is interpreted based on a predetermined rule on both sides usefully enables communication with a communication line conforming to the general wireless LAN communication standard without using a dedicated communication line.

From the functional point of view, it is not necessary to separately describe the generation apparatus side I/F 102 and the imaging apparatus side I/F 103. Both interfaces serve as a synchronization and information exchange interface for the imaging system including the radiant ray generation apparatus 108 and the radiant ray detector 104. However, the two interfaces may or may not be implemented as a product, depending on manufacturers. Therefore, description will be made on the premise that the generation apparatus side I/F 102 is a unit belonging to the radiant ray generation apparatus 108, and the imaging apparatus side I/F 103 is a unit belonging to the imaging apparatus including the radiant ray detector 104. Consequently, there is no large conceptual difference between descriptions of the imaging apparatus side I/F 103 and the generation apparatus side I/F 102. In an exemplary embodiment, for example, the connection to the imaging apparatus side I/F 103 may be replaced with the connection to the generation apparatus side I/F 102 in some cases since these interfaces have similar functions with respect to the intention of the present invention. In other words, in an exemplary embodiment, the radiant ray detector 104 may directly communicate with the switching unit B through wireless communication or wired communication.

The switching unit B may be detachably attached by using the connector 130, or simply connected and disconnected to/from the imaging apparatus side I/F 103 by using an electrical switch. Depending on the purpose of use, an operator connects or disconnects the switching unit B with the connector 130 or 131 to use or disuse an imaging unit, or selectively use a plurality of types of the imaging apparatus side I/Fs 103 (simply different interfaces or interfaces from different manufacturers). When performing imaging by using another radiant ray detector 104', it is necessary to associate the radiant ray detector 104' with the switching unit B, i.e., communication parameters exchange therebetween is required. For communication parameters exchange, for example, by connecting by cable the radiant ray detector 104' to a connector provided on the imaging apparatus side I/F 103, wireless communication parameters can be exchanged via the imaging apparatus side I/F 103. In addition, in a case where the radiant ray detector 104' and the switching unit B directly perform wireless communication, simultaneously pressing a hardware button switch provided on the radiant ray detector 104' and a hardware button switch provided on the generation apparatus side I/F 102 of the switching unit B generates a signal for exchanging wireless communication parameters to enable a handshake operation.

Figure 2:
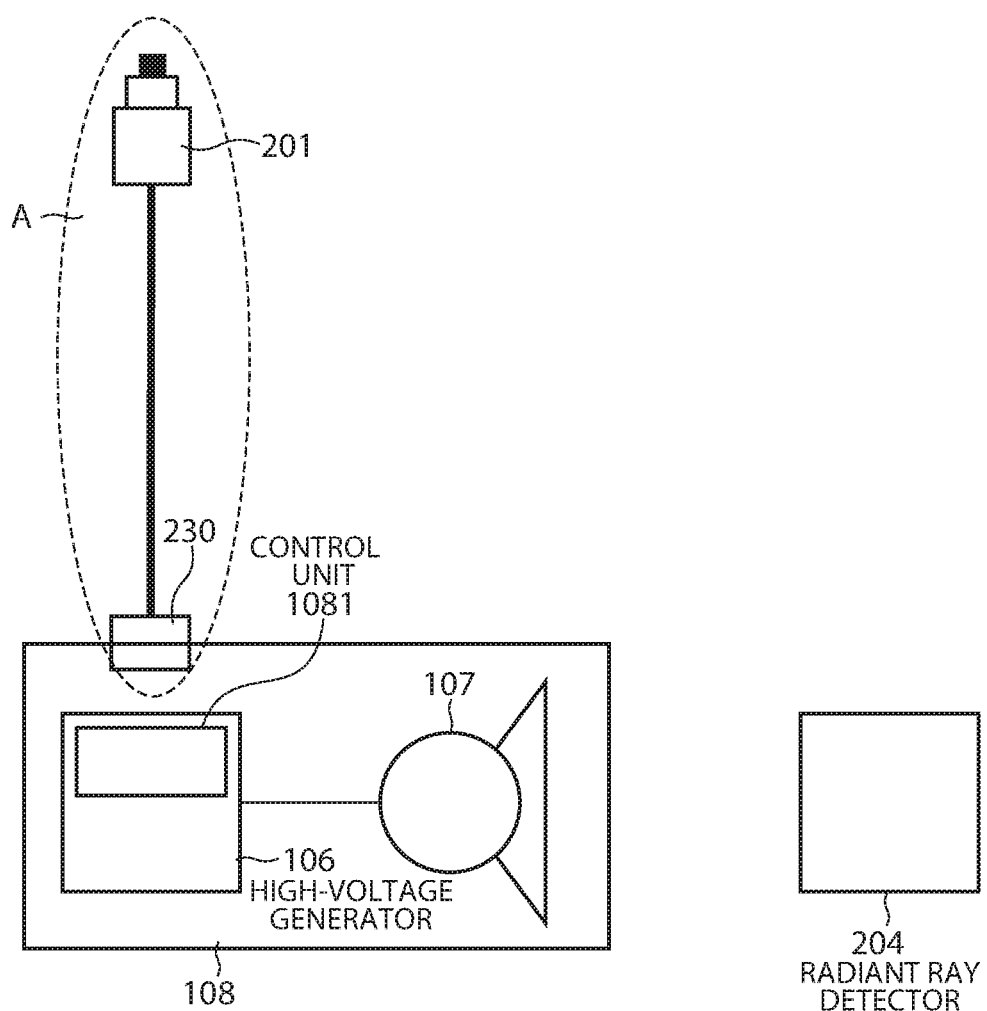
FIG. 2 is a block diagram illustrating an X-ray imaging system when a switching unit not having a synchronization interface is connected to an X-ray generator.

The following describes a case where a switching unit A which does not communicate with the imaging apparatus is connected to the radiant ray generation apparatus 108, with reference to FIG. 2. Instead of the radiant ray generation control apparatus B, an exposure switch unit A not including the connection unit 131 to connect with the radiant ray detector 104 can be connected to the connection unit on the side of the radiant ray generation apparatus 108 via a connection unit 230.

The switching unit A includes an exposure switch 201 which, when pressed, outputs the first signal indicating that the exposure switch 201 is pressed. The switching unit A is connected with the radiant ray generation apparatus 108 via the connection unit 230. When the control unit 1081 detects the output first signal, the radiant ray generation apparatus 108 performs processing for radiant ray generation preparation, such as high-voltage generation, and the radiation source 107 performs processing for radiant ray generation.

The radiant ray detector 204 used together with the radiant ray generation apparatus 108 may be, for example, a film or CR detector, or a digital radiant ray detector which does not synchronize with the radiant ray generation apparatus 108.

Of course, the radiation imaging system illustrated in FIG. 1 can also use a film or CR detector, or the radiant ray detector 104 which does not synchronize with the radiant ray generation apparatus 108. In this case, according to a setting for asynchronous mode operation, the imaging apparatus side I/F 103 is constantly outputting a signal indicating that it is ready for radiation imaging. Thus, the generation apparatus side I/F 102 acquires the relevant signal via the imaging apparatus side connection unit 131, enabling imaging similar to synchronous imaging.

In another case, referring to FIG. 1, the exposure switch 101 can be configured to be detachably attached to the generation apparatus side I/F 102. In this case, the other connection unit detachably connected to the radiant ray generation control apparatus B can be provided on the generation apparatus side I/F 102. Thus, the switching unit A illustrated in FIG. 2 can be connected directly to the connection unit of the radiant ray generation apparatus 108, or connected to the other connection unit of the generation apparatus side I/F 102. In this case, the generation apparatus side I/F 102 functions as a relaying unit (a relaying portion) for connecting the switching unit A and the radiant ray generation apparatus 108, eliminating the need of providing a plurality of exposure switches.

Further, in the above-described example, a determination unit can be provided to determine which of the radiant ray generation control apparatus B and the switching unit A is connected to the other connection unit of the radiant ray generation control apparatus B. The determination unit may be provided as an independent unit or implemented as one function of the control unit 102b. The output unit 102c outputs the result of the determination to the imaging control unit 105 and the radiant ray generation apparatus 108 via the connection unit 131 and the connection unit 130, respectively. These display control units display the result on the display unit, notifying the user of whether the radiation imaging system operates in the synchronous mode or in the asynchronous mode. In the synchronous mode, the emission timing is determined while the radiant ray generation apparatus 108 and the radiant ray detector 104 take synchronization. In the asynchronous mode, manual timing adjustment or emission detection on the side of the radiant ray detector 104 is performed.

The following describes the configuration of a radiant ray detector 304 capable of wireless communication which is an example of the radiant ray detector according to an exemplary embodiment, with reference to FIG. 3.

As illustrated in FIG. 3, the radiant ray detector 304 includes a flat panel detector (FPD) 3042 and other internal units. The FPD 3042 is configured by a combination of a scintillator composed of cesium iodide (CsI) and a two-dimensional photodetector implemented on amorphous silicon (a-Si) or single crystal silicon (Si). By using polysilicon, both sensor characteristics and easy formation of large plane can be achieved. The two-dimensional photodetector is formed of a plurality of pixels two-dimensionally arranged in matrix form. Each pixel is composed of a photoelectric conversion element and a switching element for reading charge, and is connected to a row selection line for selectively turning on the switching element and to a column signal line for transferring charges.

When X-ray enters the scintillator, it emits visible light to the two-dimensional photodetector to produce an X-ray visible light image as a result. Pixels in each row of the two-dimensional photodetector are simultaneously addressed by a line driver 3041 and the row selection line, output via the column signal line, and then held by a sample hold circuit 3043. Charge output from each pixel held by a multiplexer 3045 is amplified by an amplifier 3044, and then sequentially converted into a digital value by an analog-to-digital (A/D) converter 3046. The reading and imaging operations are controlled by a detector control unit 3049 (not illustrated). Each time the reading operation is completed for pixels on each row, the line driver 3041 sequentially drives each row on the FPD 3042. As a result, all pixels of the FPD 3042 are digitized by the above-described A/D conversion operation. The output of the A/D converter 3046 is temporarily stored in a memory 3047, and then output via a wireless communication unit 3048 in response to a request.

Before being irradiated with X-ray, the two-dimensional photodetector of the FPD 3042 performs processing for discharging a dark current accumulated in the photoelectric conversion element, etc. (initialization processing). Although the amount of accumulated dark current of the two-dimensional photodetector is proportional to time, the initialization processing is required immediately before imaging in the case of a high storage rate. When characteristics are favorable, by discharging the dark current periodically or at a suitable timing before imaging, an image having a sufficient image quality can be acquired. Further, by implementing a reset circuit for discharging in the two-dimensional photodetector, discharging can be carried out in a sufficiently shorter time than in regular discharging by the signal lines. A reset operation is performed according to an instruction of the detector control unit 3049.

The power for all of electrical components included in the radiant ray detector 1 is supplied from a battery pack 305. When the battery pack 305 is exhausted and the power cannot be supplied, the battery pack 305 needs to be replaced with a new one. To allow the user to check the remaining capacity of the battery pack 305, the detector control unit 3049 displays the total remaining capacity of the battery pack 305 or a remaining capacity warning message on a light emitting diode (LED) display provided on the battery pack 305 or an imaging unit 1, or sounds a remaining capacity warning beep by using a buzzer or speaker. These warnings prompt the user to replace the battery pack 305. To manage the remaining capacity of the battery pack 305, the user replaces the battery pack 305 by using a dedicated charging system.

The following describes signals exchanged in the radiation imaging system according to an exemplary embodiment, with reference to FIG. 4.

In the radiation imaging system according to the present exemplary embodiment, a 2-step switch is used as an exposure switch 401. A first switch signal 410 from a first switch 401a (preparation start switch, preparation switch, or prep.switch) and a second switch signal 411 from a second switch 401b (exposure switch or exp. switch) are input to a generation apparatus side I/F 402 via cables. When the generation apparatus side I/F 402 transmits to the radiant ray generation apparatus 108 the first switch signal 410 with which switch transition should occur first, the radiant ray generation apparatus 108 starts preparation for radiation emission. When the generation apparatus side I/F 402 transmits the second switch signal 411 to the radiant ray generation apparatus 108, the radiant ray generation apparatus 108, after becoming ready for radiation emission, performs radiation emission. In some cases, the exposure switch 401 may be formed of a two different switches of a sheet type such as a membrane switch on a console or a push-button switch such as a keyboard.

First, the operator adjusts the radiant ray detector 404, a subject (not illustrated), and the radiation source 107 to perform X-ray emission preparation. The generation apparatus side I/F 402 and the imaging apparatus side I/F 403 wait for respective signals. In the generation apparatus side I/F 402, the acquisition unit 402a waits for the first switch signal 410 from the exposure switch 401. The imaging apparatus side I/F 403 waits for signal 416 corresponding to a first switch from the generation apparatus side I/F 402. Then, the photographer presses the first switch 401a of the exposure switch 401. When the generation apparatus side I/F 402 receives the first switch signal 410, the output unit 402c transmits the signal 416 corresponding to the first switch, to the imaging apparatus side I/F 403 and at the same time transmits a preparation signal 414 to the radiant ray generation apparatus 108. Herein, the signal 416 corresponding to the first switch is transmitted to indicate that the first switch signal 410 does not necessarily need to be transmitted. The first switch signal 410 may also be transmitted as it is.

Immediately after the signal 416 corresponding to the first switch is transmitted, the acquisition unit 402a of the generation apparatus side I/F 402 waits for the second switch. The acquisition unit 402a may also wait for the first switch signal 410 and the second switch signal 411 in parallel. When the imaging apparatus side I/F 403 receives the signal 416 corresponding to the first switch, the radiant ray detector 404 performs an instruction for starting state transition processing. The relevant processing including various processing, such as starting bias application to the FPD 3032, turning ON the power of the processing circuit, starting idle drive, starting initialization, starting storage, and so on is performed under control of the detector control unit 3049. Immediately after the radiant ray detector 404 performs the instruction for starting state transition processing, the imaging apparatus side I/F 403 shifts to the waiting state.

When the operator presses the second switch 401b, the acquisition unit 402a of the generation apparatus side I/F 402 detects the second switch signal 411, and proceeds to the following processing. The generation apparatus side I/F 402 transmits the signal 416 corresponding to the second switch to the imaging apparatus side I/F 403. The radiant ray detector 404 performs an instruction for starting imaging unit processing. Driving control of the radiant ray detector 404 may include various processing, such as starting bias application to an internal detector, turning ON the power of the processing circuit, starting idle drive, starting initialization, and starting storage. Upon transitioning to the accumulation ready state in the processing, the imaging apparatus side I/F 403 transmits a signal indicating readyness for accumulation 413 (second signal). When the acquisition unit 402a of the generation apparatus side I/F 402 receives the signal indicating readyness for accumulation 413, the output unit 402c transmits an exposure signal 415. The radiant ray generation apparatus 108 starts radiation emission to perform radiation imaging.

Then, the radiant ray generation apparatus 108 ends X-ray emission upon release of the second switch by the operator, timeout of a storage timer in the radiant ray detector 404, or, in some cases, upon reception of an emission end signal transmitted from the radiant ray generation apparatus 108 to the radiant ray detector 404. Then, the radiant ray detector 104 reads an image. Depending on the driving control, the radiant ray detector 404 periodically reads an image, and shifts to the final X-ray image read state. Then, the radiant ray detector 404 transfers the X-ray image to the imaging control unit 405, and the imaging control unit 405 displays it.

The following describes signal states at the start of imaging with reference to the timing chart illustrated in FIGS. 5A and 5B. FIG. 5A is a timing chart when a radiant ray detector is used which can shift from the idle state, in which discharge processing is periodically performed, to the image storage state in a very short time. In the present exemplary embodiment, an exposure switch 501 includes a 2-step switch. Other elements are similar to those in the exemplary embodiment described with reference to FIG. 1. The timing chart in FIG. 5A illustrates an imaging unit driving state 573 and an X-ray generator (radiant ray generation apparatus) state 577.

Upon depression of a first switch 501a, the exposure switch 501 generates a first switch signal 571, and the acquisition unit 102a acquires the generated signal. Accordingly, the control unit 102b generates a preparation signal 575. According to the preparation signal, the control unit 1081 controls the radiant ray generation apparatus 108 to perform the rotor-up processing.

Subsequently, upon depression of the second switch 501b, the exposure switch 501 generates a second switch signal 572, and the acquisition unit 102a acquires the generated signal. Accordingly, the radiant ray detector 104 shifts from the idle driving state to the storage state. When the transition to the storage state is completed, the imaging apparatus side I/F 103 outputs a signal indicating readyness for accumulation 574 (second signal) to the generation apparatus side I/F 102. The signal indicating readyness for accumulation 574 may be generated by the imaging apparatus side I/F 103 acquiring the state of the radiant ray detector 104 or generated by the radiant ray detector 104.

Upon input of the signal indicating readyness for accumulation 574, the control unit 102b generates an exposure signal 576 and then outputs the generated signal to the radiant ray generation apparatus 108. Then, the control unit 1081 controls the radiation source 107 to generate radiant ray to start radiation emission. Radiant ray generation is carried out for a predetermined time and ended under control of the control unit 1081.

When the depression of the second switch 501b ends, the second switch signal 572 turns OFF. In this case, the acquisition unit 102a may acquire the second switch signal 572 which is turned OFF. Alternatively, the acquisition unit 102a may acquire only a signal which is turned ON and does not acquire a signal which is turned OFF.

After the second switch signal 572 turns OFF or after the predetermined storage time period has elapsed, the radiant ray detector 104 finishes the storage and then starts charge read drive. After completion of the reading operation, the radiant ray detector 104 shifts to the idle state again. The radiant ray detector 104 transmits a radiographic image based on the read charge to the imaging control unit 105. Then, the imaging control unit 105 applies predetermined image processing to the radiographic image and displays the resultant image on the display unit.

FIG. 5B is a timing chart when a radiant ray detector used performs the initialization processing when transitioning from the idle state to the storage state. As for a part of exchanged signals equivalent to those in FIG. 5A, redundant descriptions will be omitted.

In the present exemplary embodiment, when the imaging control unit 105 or the radiant ray detector 104 receives the second switch signal 572, the detector control unit 3049 controls the FPD 3042 to shift from the idle state to the initialization state. In the initialization processing, the detector control unit 3049 starts, upon reception of the second switch signal 572 as a trigger, the same processing as the periodical discharge processing performed in the idle state.

In another example, in consideration of the response to the second switch signal 572, the detector control unit 3049 reduces the reading time to be shorter than that in the initialization processing in the idle state, or, when discharge processing is repeated a plurality of times, reduces the time interval between one-unit discharge processing. The reading time can be reduced by shortening the time period during which a switching element connected with each photoelectric conversion element of the FPD 3042 is ON.

In another example, in consideration of the image quality of an image acquired through radiation emission, the time interval during which the switching element is ON is prolonged to be longer than that in the initialization processing in the idle state, or the number of times of discharge processing is increased to be larger than that in the initialization processing in the idle state, ensuring reliable discharge processing. Even in this case, the response can be improved by reducing the time interval between one-unit discharge processing. The above-described control can be achieved through signal transmission to the FPD 3042 by the detector control unit 3049.

When the initialization processing ends, the radiant ray detector 104 shifts to the storage state. In response to the shifting to the storage state, the radiant ray detector 104 transmits the signal indicating readyness for accumulation 574 (second signal) to the radiant ray generation apparatus 108. Accordingly, the control unit 102b of the generation apparatus side I/F 102 generates the exposure signal 576, and the output unit 102c outputs the generated signal to the radiant ray generation apparatus 108.

The above-described signal exchange achieves synchronization between the imaging apparatus including the radiant ray detector 104 and the radiant ray generation apparatus 108 to perform radiation imaging.

Control for achieving signal exchange illustrated in the timing chart in FIG. 5A and control for achieving signal exchange illustrated in the timing chart in FIG. 5B can be performed in each of the radiant ray generation control apparatus B, the imaging apparatus side I/F 103, the radiant ray detector 104, and the radiation imaging apparatus 105. Which control is to be performed depends on which radiant ray detector 104 is connected to the radiation imaging system.

The following describes an exemplary embodiment based on another system configuration.

Figure 6:
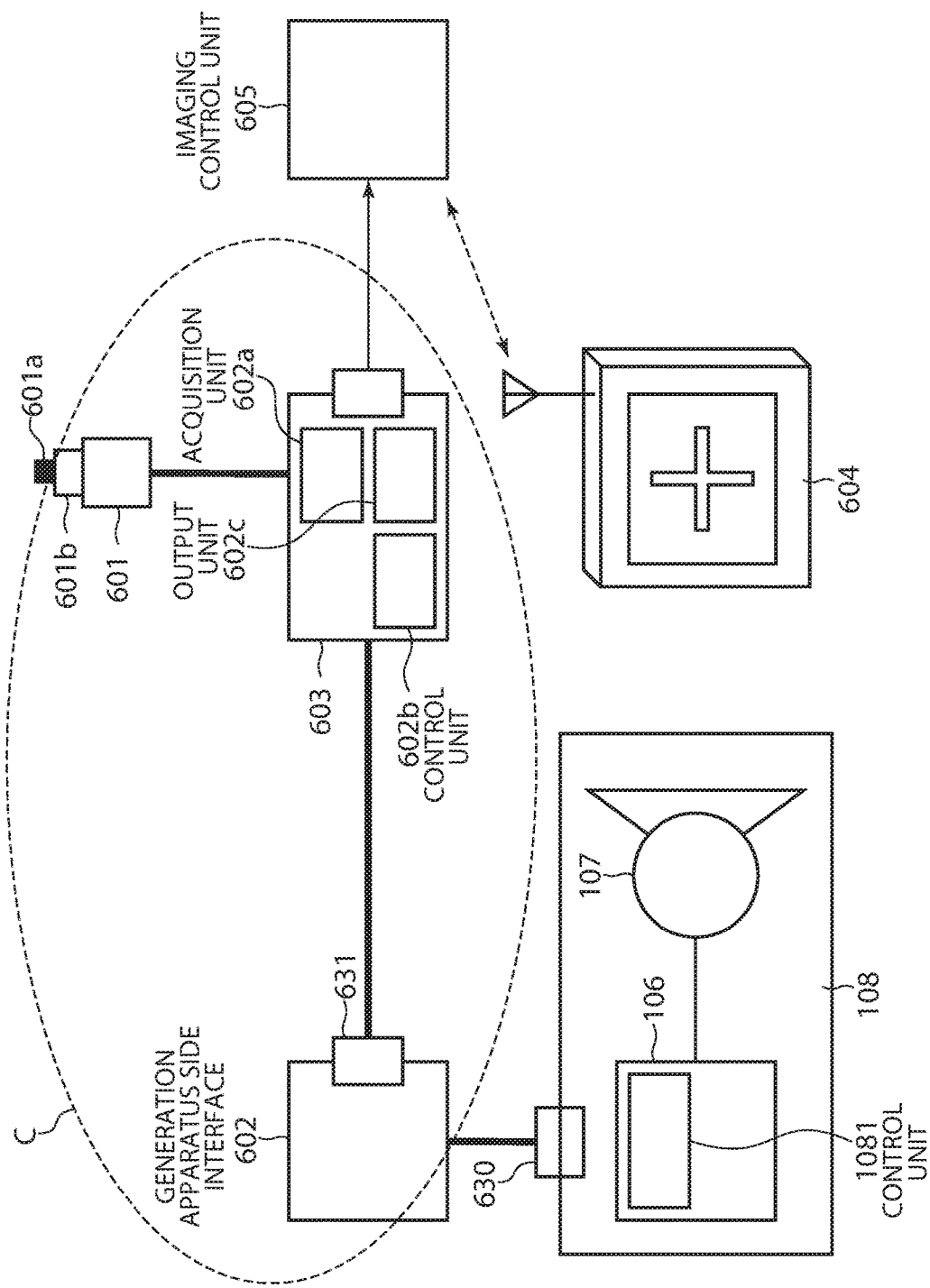
FIG. 6 is a block diagram illustrating an X-ray imaging system when other switching unit having a synchronization interface is connected to an X-ray generator via a relaying unit.

Referring to FIG. 6, an operation switch 601 is disposed in the imaging apparatus side I/F 603. For functions and configurations equivalent to those in the above-described exemplary embodiments, redundant descriptions will be omitted. An acquisition unit 603a, a control unit 603b, and an output unit 603c perform similar processing to that performed by the acquisition unit 102a, the control unit 102b, and the output unit 102c, respectively.

It is possible to remove a generation apparatus side I/F 602 and directly connect the imaging apparatus side I/F 603 to the radiant ray generation apparatus 108. However, connector shape conversion and insulation processing for ensuring safety are performed at the generation apparatus side I/F 602 in consideration of a case where units manufactured by different manufacturers are connected. In this case, the generation apparatus side I/F 602 functions as a relaying unit. The shape of a connection unit 631 of the generation apparatus side I/F 602 is intentionally differentiated from that of the connector of the radiant ray generation apparatus 108, so that a general operation switch can be prevented from being directly connected to the generation apparatus side I/F 602 supplied by a radiant ray generation apparatus maker. In insulation processing, optical elements such as photocouplers, and electromagnetic coupling by coils, and so on is used for signals of the operation switch 601 which is permitted to be connected. In a case where the power cannot be supplied from the radiant ray generation apparatus 108 to the generation apparatus side I/F 602, the power may be supplied from the imaging apparatus side I/F 603 to the generation apparatus I/F 602 side including the insulating element via an insulated power supply.

The switching unit B illustrated in FIG. 1, the switching unit A illustrated in FIG. 2, and the switching unit C illustrated in FIG. 6 are exchangeable at the generation apparatus side connection unit 130.

Types of signals to be exchanged are similar to those illustrated in FIGS. 4 and 5, and redundant descriptions will be omitted.

The following describes the radiation imaging system according to another exemplary embodiment, with reference to FIG. 7. In the present exemplary embodiment, the signal indicating that an exposure switch 701 is pressed is only monitored, and the signal indicating readyness for accumulation is not returned from the imaging apparatus. Therefore, unidirectional communication is performed between a generation apparatus side I/F 733 and an imaging apparatus side I/F 703. Although a wired signal transmission line may be used, the use of wireless communication enables imaging without being bothered by cables, improving imaging efficiency. Signals are transmitted from the generation apparatus side I/F 733 to the imaging apparatus side I/F 703. In the above-described configuration, a reception unit for receiving a signal from the imaging apparatus side I/F 703 and control for processing the received signal can be omitted, simplifying the configurations of the control unit 702b and the generation apparatus side I/F 733.

An exposure switch 701 is a remote control for transmitting a signal through wireless communication. The exposure switch 701 includes a wireless transmission unit for transmitting a signal (first signal) generated upon depression of a first switch 701a and a second switch 701b. The wireless transmission unit may be, for example, an infrared transmission unit. In this case, the acquisition unit 733 functions as a reception unit for receiving the signal (first signal) output as a wireless signal. This case enables synchronization between the digital radiant ray detector and the radiation imaging apparatus based on a simple configuration using the remote control type exposure switch 701, enabling imaging without being bothered by cables.

The present exemplary embodiment monitors exposure switch signals without substantial modifications. For example, with respect to the cables from the exposure switch 701 to the radiant ray generation apparatus 108, an acquisition unit 702a monitors the electromagnetic field of each single wire related to a first switch signal 711 and a second switch signal 712. Then, an output unit 702c transmits these switch signals to the imaging apparatus side I/F 733. In this case, if the single wire of connection cannot be taken out in advance, the acquisition unit 702a may perform signal detection by using a Hall element or coil after cable processing is performed, such as removing the exterior cover of double covering for a target signal to expose the single wire of the target signal line. In other exemplary embodiments, the generation apparatus side I/F 733 monitors the magnetic field generated by a high-voltage current generated by the high-voltage generation unit 106, detects the depression state of the exposure switch 701, for example, by using a pressure sensor stuck on the exposure switch 701, or monitors the relative position of respective operation switches (first and second switches) of the exposure switch 701.

The generation apparatus side I/F 733 performs wireless communication with the control unit 1081 of the radiant ray generation apparatus 108. In this case, the output unit 702c functions as a wireless communication unit for outputting a wireless signal. The control unit 702b performs control to output a signal for instructing radiation emission, to the radiant ray generation apparatus 108 via the output unit 702c. A generation apparatus side connection unit 730 functions as a wireless communication unit for transmitting and receiving a signal to/from the radiant ray generation apparatus 108. Wireless communication can also be achieved by connecting an infrared transmitter-receiver to the connector 130 in the above-described exemplary embodiments.

Thus, since the layout of the exposure switch 701, the generation apparatus side I/F 733, and the radiant ray generation apparatus 108 can be changed depending on situation without being bothered by cables, the present exemplary embodiment is applicable to various medical sites depending on situation.

The generation apparatus side I/F 733 may be offered by the imaging apparatus maker as an expansion unit for the imaging apparatus side I/F 703. This eliminates the need of substantially modifying the radiant ray generation apparatus 108, providing an advantage that synchronous imaging by the digital radiant ray detector 704 can be achieved with a simple configuration.

FIG. 8 illustrate an example of another exemplary embodiment, in which an infrared splitter 833d for splitting an infrared signal is provided in the generation apparatus side I/F 833 in the exemplary embodiment illustrated in FIG. 7. The infrared splitter 833d functions as a splitting unit for splitting the above-described signal (first signal) from the exposure switch 801 by partially reflecting the signal to acquire a reflection signal (third signal). The infrared splitter 833d functions also as an output unit for outputting the split signal (third signal) as a signal for shifting the radiant ray detector 804 to the radiation detectable state.

The following describes a case where the exposure switch 801 is an infrared remote control. In this case, a generation apparatus side I/F 833 receives the infrared signal of the exposure switch 801 at approximately the same time that the radiant ray generation apparatus 108 receives the infrared signal. However, the simultaneity is not strictly required. When an imaging apparatus side I/F 803 having an infrared reception unit is simply disposed in a space without a clear intention, only one of the radiant ray generation apparatus 108 and the radiant ray detector 804 receives a signal and another does not, resulting in a state where the two units are not in synchronization with each other. Therefore, the generation apparatus side I/F 833 is disposed at a position which is the same as or close to the position of the infrared reception unit 840 of the radiant ray generation apparatus 108. Further, the imaging apparatus side I/F 803 is disposed at a position close to the position of the generation apparatus side I/F 833, at which the generation apparatus side I/F 833 covers the infrared reception unit 840 so that the signal of the remote control does not directly reach the infrared reception unit 840 of the radiant ray generation apparatus 108. In this example, with the infrared reception unit 840 covered by the generation apparatus side I/F 833, the infrared splitter 833d splits the infrared signal to transmit a part of the infrared signal (transmitted infrared signal) to the infrared reception unit 840 and transmit a part thereof to the imaging apparatus side I/F 803, thus outputting the first and second switch signals to the imaging apparatus side.

Thus, synchronous imaging is achieved with a simple configuration using the wireless remote control type exposure switch 801 and the infrared splitter 833d, minimizing modifications on the side of the radiant ray generation apparatus 108.

The following describes signal exchange in a radiation imaging system performing unidirectional communication as illustrated in FIGS. 7 and 8, with reference to the timing chart illustrated in FIG. 9.

For elements overlapping with those in the timing chart illustrated in FIG. 5, redundant descriptions may be omitted. FIG. 9A is a timing chart when a radiant ray detector is used which can shift from the idle state, in which periodical discharge processing is performed similar to the timing chart illustrated in FIG. 5A, to the image storage state in a very short time, without performing the initialization processing. The following describes a radiation imaging system according to an exemplary embodiment illustrated in FIG. 7.

The control unit 702b of the generation apparatus side I/F 733 performs control to output a signal 971 (generated upon depression of the first switch 701a) to the radiant ray generation apparatus 108 via the wireless communication unit, and to output a signal 972 (generated upon depression of the second switch 701b) to the radiant ray detector 704 and the radiant ray generation apparatus 108.

First, the acquisition unit 102a acquires a first signal indicating that the exposure switch 701 is pressed. The first signal includes the first switch signal 971 generated upon depression of the first switch 701a (first switch) included in the exposure switch 701 and the second switch signal 972 generated upon depression of the second switch 701b (second switch) included therein. The acquisition unit 702a acquires and identifies the first switch signal 971 and the second switch signal 972 of the exposure switch 701. Upon depression of the first switch signal 971, the control unit 702*b* generates a preparation signal 975 and then wirelessly transmits the generated signal to the generator control unit 1081. Then, the radiant ray generation apparatus 108 performs the rotor-up processing and then performs processing for radiant ray generation preparation. When the infrared splitter 833*d* illustrated in FIG. 8 is used, the preparation signal 975 is similar to the first switch signal 971, and no delay arises in addition to signal transmission delays.

In the present exemplary embodiment, it is desirable to provide a display control unit for displaying, when the radiant ray generation apparatus 108 completes the rotor-up processing and has become ready for radiation generation, the relevant state on at least one of the generation apparatus side I/F 733 and the radiant ray generation apparatus 108. Although the display unit may be provided on at least one of the generation apparatus side I/F 733 and the radiant ray generation apparatus 108, by providing the display unit at an easily viewable position, such as the vicinity of the radiation source 107 of the radiant ray generation apparatus 108, or at a plurality of positions, the state of the radiant ray generation apparatus 108 can be confirmed. Thus, it is desirable that the photographer presses the second switch 901*b* while monitoring the state of the radiant ray generation apparatus 108. This configuration enables reducing adverse effects on the image quality resulting from a prolonged storage time period in the radiant ray detector 704.

First, upon acquisition of the second switch signal 972, the generation apparatus side I/F 733 performs control to output the switch signal to the radiant ray detector 704 via the output unit 702*c*. The signal output here may be the second switch signal 972 itself or a modified version thereof generated by the control unit 702*b* having a format interpretable by the imaging apparatus. The second switch signal 972 is handled as a signal for shifting the radiant ray detector 704 to the radiation detectable state. Upon acquisition of the second switch signal 972, the radiant ray detector 704 shifts from the idle state to the storage state.

Upon acquisition of the second switch signal 972, the generation apparatus side I/F 733 performs control to output the exposure signal to the radiant ray generation apparatus 708 via the output unit 702*c*. When the control unit 1081 receives the exposure signal, the radiant ray generation apparatus 108 generates radiant ray.

The radiant ray detector 704 in the storage state detects the generated radiant ray, and stores charges. Then, the radiant ray detector 704 completes the storage processing, and performs the read processing for reading charges from the FPD 3042 to acquire radiographic image data.

Performing processing in this way enables synchronous imaging even in a case where the radiant ray generation control apparatus B and the imaging apparatus perform unidirectional communication.

FIG. 9B is a timing chart in a case where the radiant ray detector 704 requires the initialization processing after the second switch signal 972 indicating that the second switch 701*b* is pressed reaches the radiant ray detector 704 when the idle state shift to the storage state, similar to the timing chart illustrated in FIG. 5B.

When the signal indicating readyness for accumulation 974 is not present, the generation apparatus side I/F 733 or, depending on the configuration, the imaging apparatus side I/F 703 provides a delay time equal to or longer than the initialization time since the time of generation of the second switch signal 972, and then outputs an exposure signal 976. Thus, synchronous imaging can be carried out also in the case of unidirectional communication.

Thus, X-ray imaging can be performed even without using the signal indicating readyness for accumulation 974. However, even if the first switch signal 971 is received, the radiant ray detector 704 may not shift to the accumulation ready state because, for example, patient information is not input, the radiant ray detector 704 is detective, or the imaging control unit 705 cannot receive a radiographic image, X-ray imaging cannot be stopped. Therefore, the display control unit for performing control to display on the display unit whether the radiant ray detector 704 or the imaging apparatus can shift to the storage state is to be provided on at least one of the imaging apparatus side I/F 704 and the imaging control unit 705. By providing a display unit on either one or both of the imaging apparatus side I/F 704 and the imaging control unit 705, the photographer can be notified of the state of the radiant ray detector 704, reducing the possibility of invalid radiation emission. In this case, the imaging control unit 705 can control the display control unit for displaying a radiographic image on the display unit, to display information indicating that the radiant ray detector 704 is in the storage state.

Figure 10:
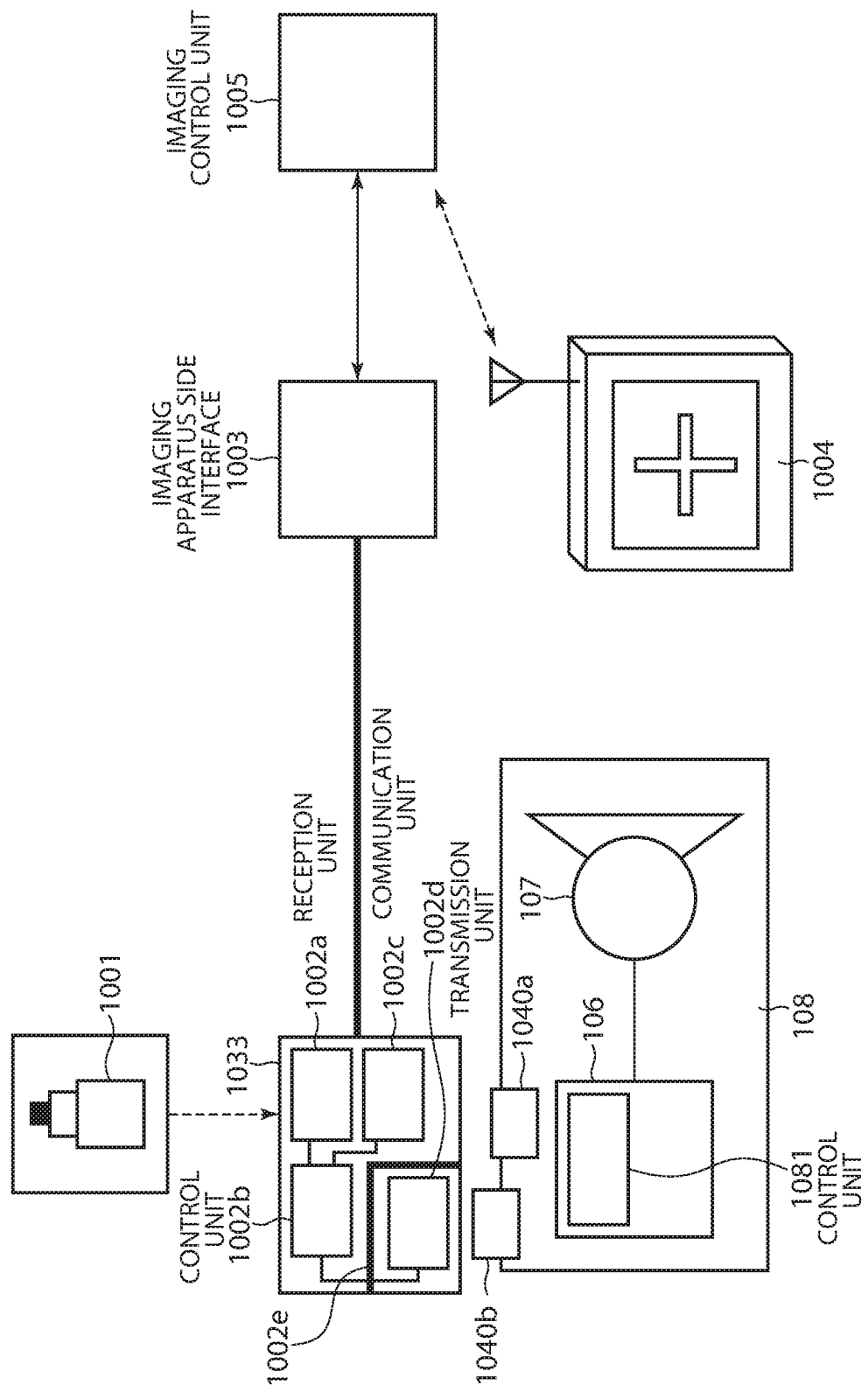
FIG. 10 is a block diagram illustrating an X-ray imaging system including a synchronization interface corresponding to a switch for wirelessly transmitting a signal.

The following describes an exemplary embodiment using an exposure switch for wirelessly outputting a signal, with reference to FIG. 10. In the present exemplary embodiment, the radiant ray generation control apparatus B and the imaging apparatus perform bidirectional communication. The radiant ray generation apparatus 108 includes a wired connection unit 1040*a* formed of a connector, and a wireless connection unit 1040*b* formed of an infrared transmitting and receiving unit.

An exposure switch 1001 is formed of an infrared remote control and the like.

A generation apparatus side I/F 1033 includes a reception unit 1002*a* for receiving an infrared signal from an exposure switch 1001, a communication unit 1002*c* for transmitting and receiving signals, and a transmission unit 1002*d*. These units correspond to the acquisition unit 102*a* and the output unit 102*c* in the above-described exemplary embodiment. A control unit 1002*b* has a similar function to that of the control unit 102*b* according to the above-described exemplary embodiment. The generation apparatus side I/F 1033 further includes a shielding member 1002*e*.

The communication unit 1002*c* performs signal exchange with an imaging apparatus side I/F 1003 by using infrared ray, a wireless LAN, or a wired connection.

The reception unit 1002*a* and the transmission unit 1002*d* perform signal exchange with the wireless connection unit 1040*b* of the radiant ray generation apparatus 108, for example, by using infrared ray.

The shielding member 1002*e* shields wireless signal reception by the wireless communication unit of the radiant ray generation apparatus 108. An acquisition unit (reception unit 1002*a*) is disposed outside the shield by the shielding member 1002*e*. The second transmission unit 1002*d* for outputting a specific signal to the wireless communication unit of the radiant ray generation apparatus 108 under control of the control unit 1002*b* is disposed inside the shield of the shielding member 1002*e*.

The control unit 1002*b* is connected as a circuit to the reception unit 1002*a*, the communication unit 1002*c*, and the transmission unit 1002*d* to perform electrical signal exchange with these units. When the communication unit 1002*c* receives a signal (second signal) indicating that the radiant ray detector 1004 has shifted to the radiation detectable state, the control unit 1002*b* performs control to output a signal for instructing radiation emission to the radiant ray generation apparatus 108 via the transmission unit 1002d functioning as a wireless communication unit.

The generation apparatus side I/F 1033 is disposed to cover the wireless transmission unit 1040b so that the wireless transmission unit 1040b comes close to the second transmission unit 1002d. Further, the second transmission unit 1002d is shielded by the shielding member 1002e. The shielding member 1002e prevents the signal from the exposure switch 1001 from directly reaching the wireless connection unit 1040b, reducing the possibility that the signal (first signal) of the exposure switch 1001 reaches only one of the radiant ray generation apparatus 108 and the imaging apparatus resulting in synchronization failure. Only the reception unit 1002a of the generation apparatus side I/F 1033 can directly receive the signal (first signal) of the exposure switch 1001. The radiant ray generation apparatus 108 of the generation apparatus side I/F 1033 may be fixed by the attached fixing member.

In the generation apparatus side I/F 1033, the communication unit 1002c generates an infrared signal after reception of the signal (first signal) by the reception unit 1002a. In this case, the communication unit 1002c is connected by cable with the imaging apparatus side I/F 1003, so that the communication reliability can be improved to further extent than in the case of wireless communication.

In the generation apparatus side I/F 1033, the second transmission unit 1002d transmits the signal of the exposure switch 1001 to the wireless connection unit 1040b. Further, depending on the case, the transmission unit 1002d may be used instead of the exposure switch 1001 as another configuration. In this case, the transmission unit 1002d performs infrared transmission and reception with the imaging apparatus side I/F 1033 and the wireless connection unit 1040b to exchange not only the signals of the exposure switch 1001 but also setting information about imaging and operation information after imaging.

The following describes signal exchange in the radiation imaging system according to an exemplary embodiment, with reference to the timing chart illustrated in FIG. 11. In the exemplary embodiment illustrated in FIG. 11A, the radiant ray detector 1004 shifts to the storage state upon depression of the first switch 1011a. The following describes the radiation imaging system according to an exemplary embodiment illustrated in FIG. 10. However, a 2-step type exposure switch 1011 is used. As for elements equivalent to those in the timing chart illustrated in FIGS. 5 and 9, redundant descriptions thereof will be omitted.

The reception unit 1002a receives a first switch signal 1171 output upon depression of a first switch 1101a. The control unit 1002b controls the communication unit 1002c to output, upon reception of the signal 1171 of the first switch 1101a (first switch), a signal for shifting the radiant ray detector 1004 to the radiation detectable state. In the present exemplary embodiment, the communication unit 1002c outputs the first switch signal 1171 as it is.

The detector control unit 3049 of the radiant ray detector 1004 performs control to sequentially repeat the discharge and storage states upon reception of a signal from the radiant ray generation control apparatus B. Then, the wireless communication unit 3048 of the radiant ray detector 1004 functions as an output unit for outputting, when a state transitions to the storage state, a signal (second signal) indicating that the radiant ray detector 1004 has shifted to the radiation detectable state. In this case, the radiant ray detector 1004 needs to periodically perform the initialization processing since continuing the storage state causes storage of the dark current component in the photoelectric conversion element. Then, immediately before the storage time period has elapsed, the detector control unit 3049 turns OFF a signal indicating readyness for accumulation 1174 to control the wireless transmission unit 3048 to stop outputting the signal indicating readyness for accumulation 1174 (second signal). Alternatively, the wireless transmission unit 3048 may transmit a signal indicating that the signal indicating readyness for accumulation 1174 is OFF. This storage time period is set so that an image having a sufficient image quality can be acquired regardless of the X-ray emission timing.

When the reception unit 1002a receives the signal generated upon depression of the second switch 1101b and the signal indicating readyness for accumulation 1174 (second signal) indicating that the radiant ray detector 1004 has shifted to the radiation detectable state, the control unit 1002b controls the transmission unit 1002d to output an exposure signal 1176 for instructing radiation emission to the radiant ray generation apparatus 108.

Once the reception unit 1002a receives the first switch signal 1171 from the radiant ray generation apparatus 108, the radiant ray detector 1004 repeats the storage and initialization processing until a second switch signal 1172 is pressed, and returns the signal indicating readyness for accumulation 1174 during the storage state. When the reception unit 1002a simultaneously receives the signal indicating readyness for accumulation 1174 and the second switch signal 1172 upon depression of the second switch 1101b, the control unit 1002b generates the exposure signal 1176. If the second switch 1101b is pressed during the initialization processing, the radiant ray detector 1004 completes the initialization processing, shifts to the storage state, and outputs the signal indicating readyness for accumulation 1174. When the reception unit 1002a receives the signal indicating readyness for accumulation 1174, the control unit 1002b generates the exposure signal 1176. This processing enables reducing the signal exchange between the radiant ray generation apparatus 108 and the imaging apparatus after the second switch 1101b is pressed. Specifically, unidirectional transmission from the imaging apparatus enables reducing the signal exchange immediately before radiation emission.

In this case, since a display unit for displaying the storage state of the radiant ray detector 1004 on the imaging control unit 1005, the generation apparatus side I/F 1033, the imaging apparatus side I/F 1003, and a display control unit for controlling the display unit are provided, it becomes easier for the user to determine imaging timing while avoiding the initialization processing. Further, since the time period until the radiant ray detector 1004 completes the storage state is displayed on a countdown method via the display control unit of the imaging control unit 1005, it becomes easier for the photographer to grasp the storage end timing, further making it easier to determine imaging timing.

When a radiant ray detector 1204 repeats the initialization processing and the storage time period in the idle state, it performs an operation as illustrated with FIG. 11B (described below). When repeating the initialization processing and the storage time period in the idle state, in consideration of the stability of the image quality of the sensor, the detector control unit 3049 can perform control to set a shorter storage time period before the first switch signal 1171 is triggered than a time period after the signal is triggered. Further, when the detector control unit 3049 performs control to provide a longer storage time period before the first switch signal 1171 is triggered than that after the signal is triggered, the ON/OFF interval of the switching element can be extended and accordingly the degradation of the FPD 3042 can be delayed, thus prolonging the useful life.

FIG. 11B is a timing chart when the radiant ray detector 1004 requires the initialization processing after the second switch signal 1172 indicating that the second switch 1101b is pressed reaches the radiant ray detector 1004 when the idle state transitions to the storage state, similar to the timing chart illustrated in FIG. 5B. Referring to FIG. 11B, when the first switch signal 1171 is triggered, the radiant ray detector 1004, remaining in the idle state, starts outputting the signal indicating readiness for accumulation 1174 to the radiant ray generation apparatus 108. The display control unit of the imaging control unit 105, 405, 605, 705, 805, 1005, 1205, 1305, 1805 controls the display unit to display the state where the signal indicating readiness for accumulation 1174 is being output, allowing the photographer to determine imaging timing.

Figure 12:
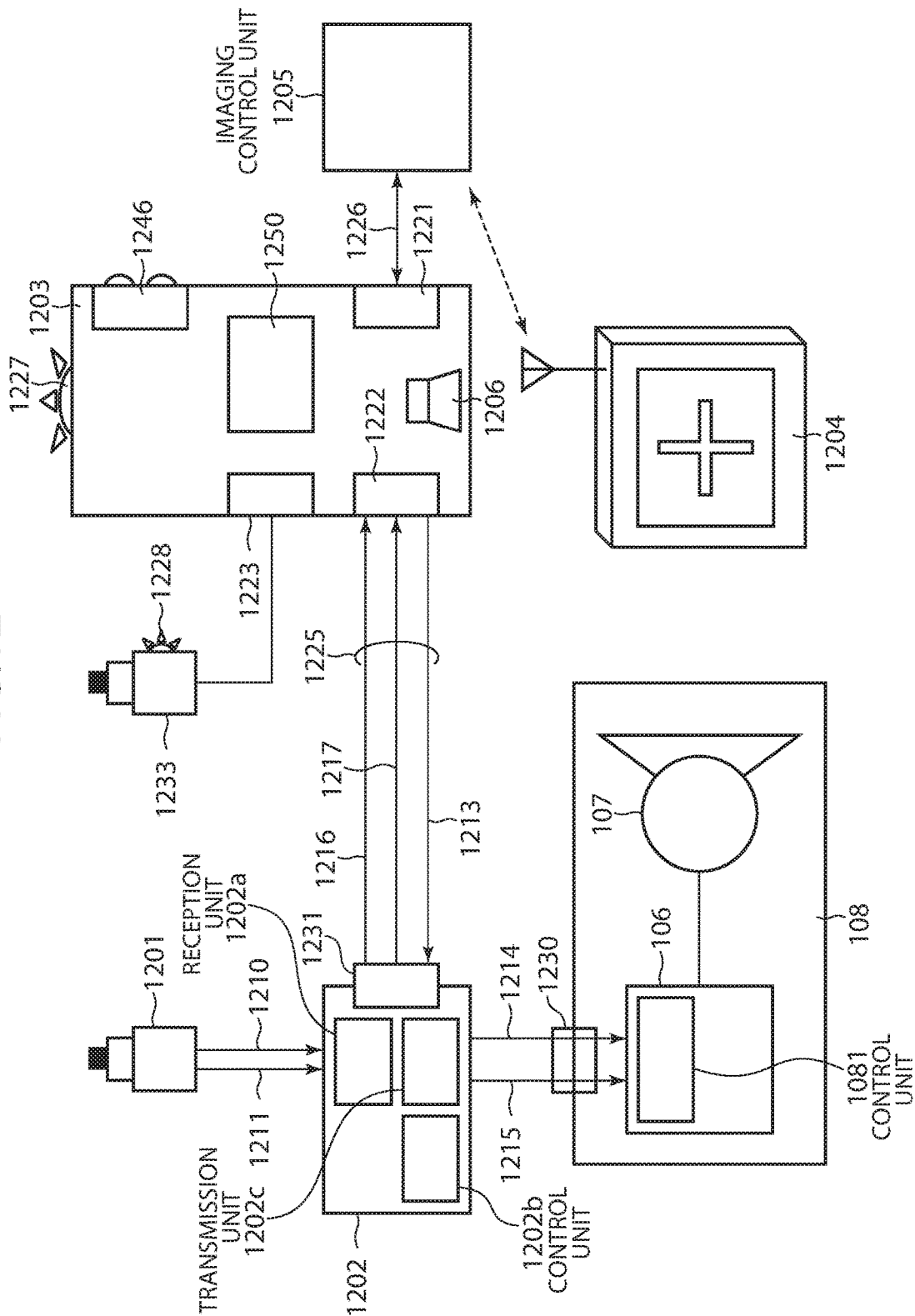
FIG. 12 illustrates an example of an interface configuration of an X-ray detector.

The following describes a configuration of a control apparatus 1203 according to another exemplary embodiments of the imaging apparatus side I/F according to an exemplary embodiment, with reference with reference to FIG. 12. As for elements equivalent to those in the above-described exemplary embodiment, redundant descriptions may be omitted. A reception unit 1202a, a control unit 1202b, and a transmission unit 1202c of a generation apparatus side I/F 1202 have similar functions, for example, to those of the acquisition unit 102a, the control unit 102b, and the output unit 102c, respectively, according to the exemplary embodiment illustrated in FIG. 1.

The control apparatus 1203 functions as an imaging apparatus side I/F for synchronizing with the radiant ray generation apparatus 108 similar to the above-described exemplary embodiments. The control apparatus 1203 also functions as an apparatus for transmitting communication parameters (check-in) for establishing communication to make the radiant ray detector 1204 operative in the radiation imaging system. Each unit of the control apparatus 1203 is comprehensively controlled by a control unit 1250.

The control apparatus 1203 includes a first wireless communication unit 1222 for wirelessly receiving a wireless communication parameter request from the radiant ray detector 1204. The first wireless communication unit 1222 also functions as a transmission unit for wirelessly transmitting wireless communication parameters to the radiant ray detector 1204.

An imaging control unit 1205 and the radiant ray detector 1204 establish connection based on wireless communication parameters received from the control apparatus 1203.

Communication between the control apparatus 1203 and the imaging control unit 1205 is established in advance, for example, by a second wireless communication unit 1221. The establishment of communication includes control processing for achieving information exchange based on a common identifier (ID), for example, when a wireless LAN is used for communication. The control apparatus 1203 and the generation apparatus side I/F 1202 establish communication in advance, for example, via the first wireless communication unit 1222. For example, when infrared communication is used, the establishment of communication includes processing for storing infrared light-emitting patterns to be output from the connection unit 1231 of the generation apparatus side I/F 1202, and the first wireless communication unit 1222, in respective reception units. The establishment of communication may further include processing for adding to infrared signals an ID indicating that each signal is coming from each apparatus.

Thus, connection between the radiant ray detector 1204 and the second wireless communication unit 1221 is established via the imaging control unit 1205.

When the radiant ray detector 1204 is registered in the radiation imaging system in this way, the radiant ray detector 1204 becomes operative in the radiation imaging system.

The first wireless communication unit 1222 receives, for example, an infrared signal and transmits wireless LAN communication parameters by using infrared ray. This function is used in operations for setting wireless communication and further additionally registering a radiant ray detector to be added to or replaced with the radiant ray detector 1204 before the establishment of wireless communication (regularly wireless LAN communication) between the radiant ray detector 1204 and the imaging control unit 1205 based on other methods.

The control apparatus 1203 includes a second wireless communication unit 1221 functioning as a second wireless reception unit and a second wireless transmission unit for communicating with the radiant ray detector 1204 based on wireless communication parameters. A wireless communication unit 1247 includes, for example, a communication module and an antenna capable of wireless-LAN-based communication.

The control apparatus 1203 achieves synchronous imaging in synchronization with the radiant ray generation apparatus 108 via the first and second communication units used for check-in and in communication with the radiant ray detector 104. Specifically, the first wireless communication unit 1222 receives from the generation apparatus side I/F 1202 signals 1216 and 1217 indicating that an exposure switch 1201 (imaging instruction switch) is pressed. The second wireless communication unit 1221 functioning as a second wireless transmission unit transmits a signal for shifting the radiant ray detector 1204 to the radiation detectable state. The second wireless communication unit 1221 functioning as a second wireless reception unit receives a signal indicating that the radiant ray detector 1204 has shifted to the radiation detectable state. The first wireless communication unit 1222 functioning as a first wireless transmission unit transmits to the generation apparatus side I/F 1202 a signal 1213 indicating that the radiant ray detector 1204 has shifted to the radiation detectable state. The radiant ray generation control apparatus B includes the generation apparatus side I/F 1202 and, depending on the case, an exposure switch 1202.

By using the first wireless communication unit 1222 (used for check-in) also for synchronous imaging, synchronous imaging can be performed by the radiant ray detector 1204 which performs wireless communication with a simple configuration. Further, by wirelessly connecting the radiant ray detector 1204 and the generation apparatus side I/F 1202 each unit can be advantageously disposed without being bothered by cables. It is also possible to provide an infrared transmission unit 1246 in addition to the first wireless communication unit 1222, and use the infrared transmission unit 1246 as a communication unit for synchronous imaging.

A 2-step switch including a first switch 1201a and a second switch 1201b is applicable as the exposure switch 1201. In this case, the first wireless communication unit 1222 receives a signal 1210 generated upon depression of the first switch 1201a (first switch) of the exposure switch 1201 (imaging instruction switch) and a signal 1211 generated upon depression of the second switch 1201b (second switch) of the exposure switch 1201 (imaging instruction switch). In this case, for example, the control illustrated in the timing chart in FIG. 11 is applicable. Specifically, the control apparatus 1203 controls the radiant ray detector 1204 to periodically repeat the initialization processing and the storage state from the idle state in response to the signal 1210 and, only while it is in the storage state, the radiant ray detector 1204 continues transmitting the signal indicating readiness for accumulation 1174 from the wireless communication unit 3048.

Further, the control apparatus 1203 can connect an imaging apparatus switch 1233 (other imaging instruction switch) by using a connector 1223. The imaging apparatus switch 1233 is provided for a situation where synchronous imaging is not possible, for example, communication with the radiant ray generation apparatus 108 cannot be appropriately performed. The control unit 1250 detects the depression of the imaging apparatus switch 1233 by acquiring a signal generated upon depression thereof. Then, the control unit 1250 outputs an instruction for shifting the radiant ray detector 1204 from the idle state to the storage state.

In this case, the first wireless communication unit 1222 used for check-in is used not only for synchronous imaging but also for receiving, after radiation emission, from a radiation control apparatus parameters regarding the radiant ray generated by the radiant ray generation apparatus 108. After radiation emission, the control unit 1081 of the radiant ray generation apparatus 1081 transmits radiant ray generation operation information including the tube current, the mAs value, etc., to the generation apparatus side I/F 1202 via an infrared transmitting and receiving unit 1230. Then, the generation apparatus side I/F 1202 transmits the operation information to the first wireless communication unit 1222, for example, by using infrared ray. If the control unit 1250 of the control apparatus 1203 transmits the operation information to the imaging control unit 1205 via the second wireless communication unit 1221, the imaging control unit 1205 can associate the radiographic image data acquired from the radiant ray detector 1204 with the operation information, and use the relevant data for diverse image processing.

The control apparatus 1203 does not need to be directly connected to the imaging control unit 1205 but connected to the radiant ray detector 1204 directly to an access point or indirectly via the access point. In one exemplary embodiment, the control apparatus 1203 connects by cable with the generation apparatus side I/F 1202 via a connection line 1225, and also connects with the imaging control unit 1205 via a connection line 1226. When the control apparatus 1203 and the generation apparatus side I/F 1202 are to be disposed close to each other, the use of wired connection ensures stability and certainty of communication without sacrificing convenience. Further, by performing wired communication and supplying the power via the connection lines 1225 and 1226, a highly reliable system can be built.

When wireless communication is employed, a battery is provided as a power supply for the control apparatus 1203 and generation apparatus side I/F 1202. As a wired connection method, by using a command-based general-purpose interface, such as Recommended Standard 232C (RS232C) and Universal Serial Bus (USB), a radiation imaging system can be built more easily than using dedicated lines. As a wireless connection method, a general-purpose interface, such as the wireless LAN standard, Bluetooth (registered trademark), and Infrared Data Association (IrDA) communication, is applicable. A customized interface including an additional unique communication protocol in the above methods is also applicable. By applying a USB connection, serving as both a general-purpose communication interface and a power supply line, to the line 1226 connecting with the imaging control apparatus 1205, not only versatile command-based communication can be easily implemented but also the power can be supplied from the imaging control unit 1205, which improves convenience.

Further, the control apparatus 1203 can be provided with a LED 1227 for displaying a plurality of statuses, such as the accumulation ready state of the radiant ray detector 1204 and the battery state. In this case, under control of the control unit 1250, the LED 1227 lights up when the radiant ray detector 1204 has shifted to the storage state. Alternatively, the control apparatus 1203 may be provided with a display instead of the LED 1227, or with a sound source 1206 for notifying the state of the imaging unit. These notifications are controlled by the control unit 1250.

Alternatively, if an information unit for notifying the state of the radiant ray detector 1204 is provided in the housing of the exposure switch 1201 held by the photographer at the time of radiation emission, the photographer can be notified of the state of the radiant ray detector 1204 in an easily viewable way. Since the exposure switch 1201 is held by hand of the photographer, it is not appropriate to provide the information unit on a portion held by hand or pushed by finger. Further, considering that the exposure switch 1201 may be used with either hand, it is desirable that the upper surface around the switches of the exposure switch 1201 lights up.

The control apparatus 1203 can also be configured as a unit mounted with an interface applicable to the above-described plurality of exemplary embodiments. In this case, the system operation including the operation of the radiant ray detector 1204 changes depending on a setting. The control unit 1250 for controlling all of the above-described changeover operations may be configured to control all of units or configured mainly for interface conversion. In the latter case, the control unit 1250 may commit a part or whole of main control to the detector control unit 3049 in the imaging control unit 1205 or in the radiant ray detector 1204.

The following describes the operation in a case where the exposure switch 1201 is an infrared remote control. The infrared remote control of the exposure switch 1201 may be connected by cable to the control apparatus 1203. Further, the control apparatus 1203 is integrally configured with the generation apparatus side I/F 1202.

First, the light-emitting patterns (the first switch signal 1211, the second switch signal 1212, the collimator lighting signal, etc.) of the infrared remote control for the radiant ray generation apparatus 108 are stored in the control apparatus 1203 or the imaging control unit 1205 via the wireless reception unit 1245. Then, the infrared transmission unit 1246 is disposed to face the infrared reception unit 1230. In this case, the infrared reception unit 1230 may be entirely covered by a unit including the control apparatus 1203 to prevent the infrared reception unit 1230 from being operated by any other infrared remote controls. Conversely, to make use of the operation of the exposure switch 1201 on an infrared unit of the radiant ray generation apparatus 108, arrangement may be made so that the opening of the infrared reception unit 1230 is not blocked as much as possible to allow the operator to freely operate both switches of the exposure switch 1201 without any changeover operation. Then, the wired exposure switch 1201 of the radiant ray generation apparatus 108 is removed, or another exposure switch 1233 having a similar function is prepared and attached to the control apparatus 1203 via the connection unit 1223. Then, when the operator activates the entire radiation imaging system and then presses the first switch of the exposure switch 1201 attached to the control apparatus 1203, the wireless transmission unit 1246 transmits a preparation signal 1214 to the infrared reception unit 1230 by using infrared ray. At the same time, the radiant ray detector 1204 performs preparation processing as required. Then, after the operator presses the second switch and the radiant ray detector 1204 completes preparation processing, the infrared transmission unit 1246 transmits an exposure signal 1215 to the infrared reception unit 1230. In this configuration, if an image acquisition system of the radiant ray detector 1204 and the imaging control unit 1205 cannot acquire an image because of a certain reason (for example, patient information is not input or the power is not turned ON) when the operator operates the exposure switch 1201, the infrared transmission unit 1246 emits no infrared signal, reducing events involving useless X-ray emission.

Further, there may be provided functions convenient for diagnosis, such as a USB extended HUB function for data exchange and a barcode reader. When unidirectional communication is applied as in the exemplary embodiments illustrated in FIGS. 7 and 8, communication with the radiant ray detector 1204 may be achieved only by the wireless transmission unit 1246.

When the exposure switch 1233 is connected by cable to the control apparatus 1203, it can be used as a trigger switch for shifting the radiant ray detector 1204 to the storage state upon depression of the switch 1233. This case has an advantage that X-ray will not be accidentally emitted while the radiant ray detector 1204 is not ready for storage operation because of a certain reason, regardless whether the operator is careful or not.

When the radiation imaging system is actually operated in a hospital, the radiant ray detector 1204, the imaging control unit 1205, and the control apparatus 1203 may not be preinstalled in the mobile radiant ray generation apparatus 108. In this case, each time the radiation imaging system is used, the radiant ray detector 1204, the imaging control unit 1205, and, depending on the case, the control apparatus 1203 are to be installed in or attached to the mobile radiant ray generation apparatus 108. In consideration that handling of cables tends to be complicated, the control apparatus 1203 is provided with sucking discs or a hold function to ensure stable operations at the time of cable connection and disconnection.

The following describes an exemplary embodiment of a radiation imaging system provided with a switch different from the exposure switch, with reference to FIG. 13. Referring to FIG. 13, an expansion unit 1333 of an imaging apparatus side I/F 1303 includes an independent switch, and is attached to cover an exposure switch 1301. When providing the switch on the expansion unit 1333, the switch is disposed so that the timing at which the operator operates the second switch of the exposure switch 1301 is detected at approximately the same time. For example, an operation button having an repulsive force intermediate between repulsive forces of the first and second switches may be provided on the exposure switch 1301 and pressed at approximately the same time as the second switch. Further, an interlock mechanism may be provided to prevent the depression of the exposure switch 1301 when the radiant ray detector 704 is not ready for radiation imaging. Thus, when the imaging apparatus side I/F 1303 is disposed on the exposure switch 1301 in this way, handling of the exposure switch 1301 becomes inconvenient because of doubled wires. Therefore, since a curled cable is regularly used for the exposure switch 1301, the curl cable may be desirably arranged. Further, a roll-up cable having an automatically expanding and contracting an exposed cable portion may be used.

FIG. 14 illustrates another exemplary embodiments of the expansion unit 1333 illustrated in FIG. 13.

In a radiant ray generation control apparatus including an exposure switch 1401, and an expansion unit 1433 having a storage switch, a first switch 1401a of the exposure switch 1401 outputs a signal (first switch signal or preparation signal) 1310 for instructing radiant ray generation preparation to the radiant ray generation apparatus 108. A second switch 1401b of the exposure switch 1401 outputs a signal (second switch signal or exposure signal) 1311 for instructing radiation emission to the radiant ray generation apparatus 108. The expansion unit 1433 includes an interlock unit 1455 for restricting the depression of the second switch 1401b. The expansion unit 1433 further includes an acquisition unit 1402a functioning as a communication unit for communicating with a radiant ray detector 1304, and an output unit 1402c. The expansion unit 1433 further includes a control unit 1402b for canceling a restriction imposed by a restriction member upon reception of a signal indicating that the radiant ray detector 1304 has shifted to the radiation detectable state, via the communication unit. The radiant ray generation control apparatus further includes a storage switch 1409 (third switch). Upon depression of the storage switch 1409, the output unit 1402c transmits a signal for shifting the radiant ray detector 1304 to the radiation detectable state.

The storage switch 1409 can be disposed to cover at least one of the first switch 1401a and the second switch 1401b by modifying the configuration illustrated in FIG. 14. In this case, for example, the storage switch 1409 is pressed upon depression of the first switch 1401a or upon depression of the second switch 1401b. Thus, the operator can certainly instruct the radiant ray detector 1401a with the same operability as when operating the exposure switch 1401.

Further, the storage switch 1409 is disposed to cover the second switch 1401b so that the magnitude of the pressing force of the storage switch 1409 is intermediate between the the pressing force of the first switch 1401a and the pressing force of the second switch 1401b. The switch member is selected so that such repulsive force is produced. With this configuration, the first switch 1401a is pressed and then the storage switch 1409 is pressed during the depression operation of the second switch 1401b.

As illustrated in FIG. 14, the storage switch 1409 can be disposed so that its depression direction differs from that of the first switch 1401a and the second switch 1401b, reducing the possibility that the exposure switch 1401 and the storage switch 1409 are pressed in mistake.

By providing a display unit on the exposure switch 1401 or the expansion unit 1433, the state of the radiant ray detector 1304 can be displayed in an easily viewable way for the operator. In this case, the control unit 1402b of the expansion unit 1433 performs display on the display unit showing that the acquisition unit 1402b has received the signal indicating that the radiant ray detector 1304 has shifted to the radiation detectable state.

In addition, the expansion unit 1433 functions as a supporting member for supporting the interlock unit 1455 functioning as a restriction member. The expansion unit 1433 further includes an attachment jig 1435 functioning as a fixing member for fixing the expansion unit 1433 to the exposure switch 1401.

The storage switch 1409 will be described below as a switch attached to the expansion unit 1433 of an imaging apparatus side I/F 1403. The storage switch 1409 is composed of a housing (having a weight and a size which can be held by hand), at least one switch (push button, membrane switch, etc.) for giving an instruction to the radiant ray detector 1304, and a cable or a wireless communication unit for connecting with the imaging apparatus side I/F 1403 or the radiant ray detector 1304. The storage switch 1409 issues an instruction directly related at least to an operation in the radiant ray detector 1304, such as starting storage operation of the radiant ray detector 1304 (described below). In particular, when achieving synchronization between the radiant ray generation apparatus 108 and the radiant ray detector 1304 by using an operation of the exposure switch 1401, the storage switch 1409 may be formed of a 2-step switch including the first and second switches similar to the exposure switch 1401.

Referring to FIG. 14, the expansion unit 1433 of the imaging apparatus side I/F 1303 is an independent switch, and simply attached to the exposure switch 1401 by using the attachment jig 1435. The attachment jig 1435 fixes the expansion unit 1433 by holding the cylindrical portion of the exposure switch 1401. It is desirable that the attachment jig 1435 is simply configured to be attached to various types of the exposure switches 1401. Accordingly, the attachment jig 1435 is configured not to be attached to various types of commercial exposure switch buttons but only to absorb differences in external shape of the cylindrical portion existing on almost all exposure switches. More specifically, the winding portion of the attachment jog 1435 having a variable length enables attaching it to the cylindrical portion. When providing the switch on the expansion unit 1433, the switch is disposed so that the timing at which the operator operates the second switch 1401*b* of the exposure switch 1401 is detected at approximately the same time. Alternatively, when the operator operates the second switch 1401*b* of the exposure switch 1401, the operator may press the switch on the expansion unit 1433 at approximately the same time as the second switch 1401*b*. In this case, the depression direction of the exposure switch 1401 is differentiated from the depression direction of the storage switch 1409 on the expansion unit 1433. For example, regularly, the exposure switch 1401 is formed to be operated by the thumb, and the storage switch 1409 on the expansion unit 1433 is formed to be operated by the forefinger. Forming the two switches to be easily operated by two different fingers of one hand allows the user to explicitly control operations of the two switches. The interlock unit 1455 may be provided to restrict the depression of the exposure switch 1401 by preventing it from being pressed when the radiant ray detector 1304 is not ready for radiation imaging. Referring to FIG. 14, when the radiant ray detector 1304 is not ready for radiation imaging, the interlock unit 1455 is set at a position for preventing the depression of the second switch 1401*b* of the exposure switch 1401. When the radiant ray detector 1304 is ready for radiation imaging, the interlock unit 1455 is retracted into the expansion unit 1433. The restriction of the interlock unit 1455 is cancelled upon reception of a signal from the radiant ray detector 1304. As another example, the storage switch 1409 itself may be provided on the expansion unit 1433 with an interlock mechanism for preventing depression thereof when the radiant ray detector 1304 is not ready for radiation imaging, and allowing depression thereof only when the radiant ray detector 1304 is ready for radiation imaging. Primarily, as long as the operator is not troubled, the expansion unit 1433 of the imaging apparatus side I/F 1403 may be independent switches separately disposed. In this case, the operator can operate respective switches with one hand without problem, and one of these may be a foot switch or a touch-panel button on the display on the imaging control unit 1405. Further, this button may be configured to be clicked with a mouse (example of operation unit) belonging to the imaging control unit 1405. In this case, a dark current is accumulated in the sensor even after the radiant ray detector 1304 has become ready for radiation imaging, causing a problem that the dynamic range decreases with time or the power consumption increases. Accordingly, after a predetermined time period has elapsed, the interlock unit 1455 is protruded again to be set at a position for preventing the depression of the second switch 1401*b*. Thus, if a problem of image quality degradation arises even after the radiant ray detector 1304 has become ready for radiation imaging, radiation emission can be inhibited. In addition, the function of the expansion unit 1433 may be integrated with the function of the exposure switch 1401. In this case, the function of the storage switch 1409 is integrated with the function of the first switch 1401*a*. Specifically, upon depression of the first switch 1401*a*, the expansion unit 1433 instructs the radiant ray detector 1304 to be ready for radiation imaging as described above. Upon reception of a signal indicating that the radiant ray detector 1304 has become ready for radiation imaging, the expansion unit 1433 retracts the interlock unit 1455. In this case, after the radiant ray detector 1304 starts the storage operation, the sooner radiation emission starts, the more advantageous to both image quality and power consumption. Then, after the depression of the first switch 1401*a*, upon completion of the rotor-up processing of the radiant ray generation apparatus 108, i.e., when it has become ready for radiation emission, the expansion unit 1433 instructs the radiant ray detector 1304 to be ready for radiation imaging. This alleviates a problem that the radiant ray detector 1304 shifts to the storage state immediately after the depression of the first switch 1401*a* and the image quality degrades in the case of slow rotor-up processing of the radiant ray generation apparatus 108.

The following describes signal exchange performed by the radiation imaging system including the exposure switch 1401, and the imaging apparatus switch 1233 or the storage switch 1409 for controlling the radiant ray detector 1304 of the imaging apparatus according to an exemplary embodiment, with reference to the timing chart illustrated in FIG. 15. For convenience, descriptions will be made based on the radiation imaging system according to an exemplary embodiment illustrated in FIG. 14.

Figure 15B:
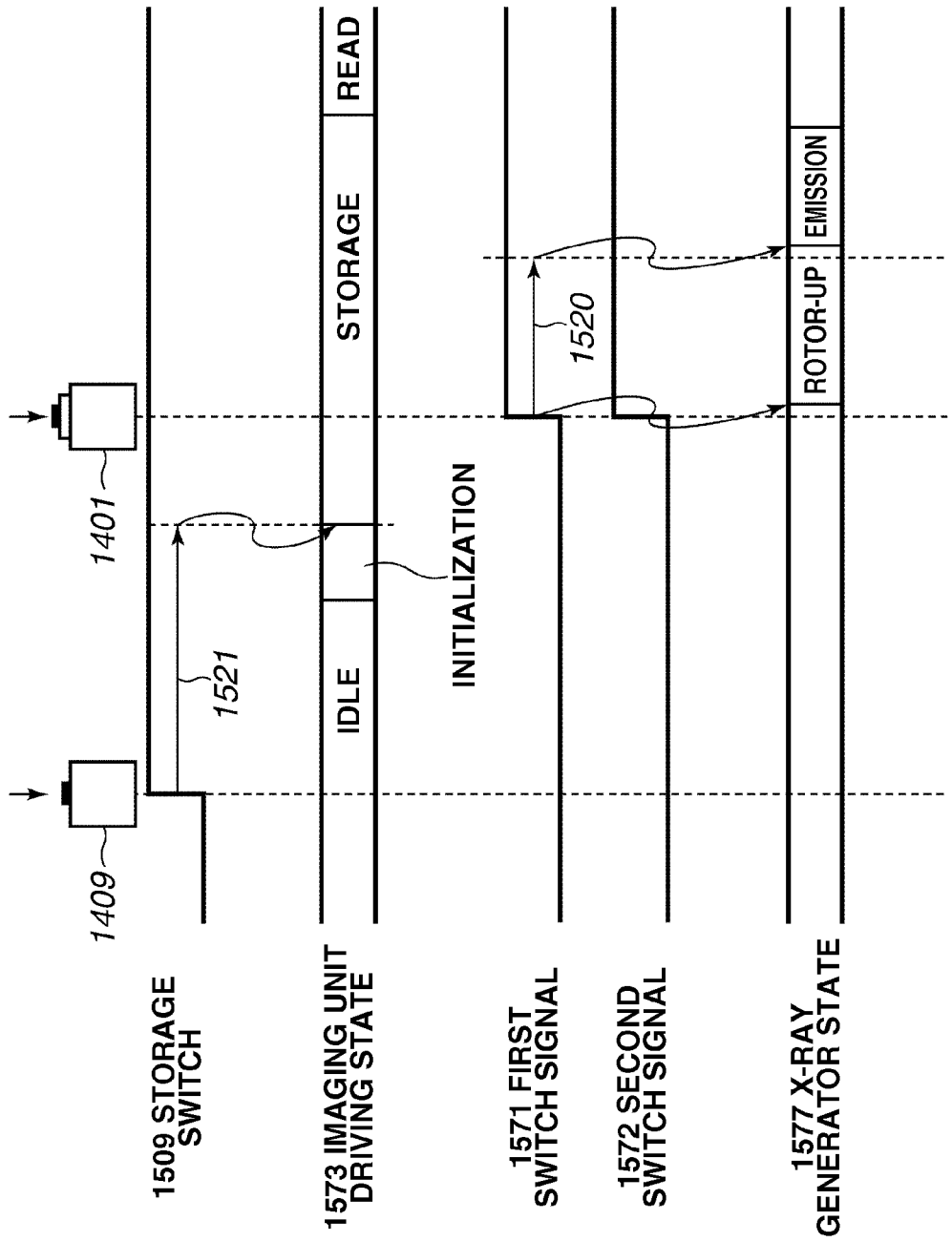
FIG. 15B is a timing chart illustrating control according to still another exemplary embodiment.

The following describes an operating sequence when the storage switch 1409 is provided on the expansion unit 1433 of the imaging apparatus side I/F 1403. Referring to FIGS. 15A and 15B, the storage switch 1409 is a switch attached to the expansion unit 1433 of the imaging apparatus side I/F 1403. Referring to FIG. 15A, after the X-ray generator state 1577 has shifted to the ready state with only the first switch 1401*a* of the exposure switch 1401 pressed, i.e., with a signal 1571 of the first switch 1401*a* turned ON, the operator presses the storage switch 1409. When initialization is required, an imaging unit driving state 1573 shifts to the storage state after initialization. Otherwise, the imaging unit driving state 1573 immediately shifts to the storage state. While the imaging unit driving state 1573 is in the storage period, the operator presses the second switch 1401*b* of the exposure switch 1401. Then, the X-ray generator emits X-ray in the X-ray generator state 1577. In this case, the imaging unit driving state 1573 needs to be kept in the storage state until X-ray emission ends. Conversely, X-ray emission needs to be ended before the storage state ends.

Referring to FIG. 15B, the operator presses a storage start switch 1509 at the beginning of the sequence. Then, after a countdown period 1521 has elapsed, the imaging unit driving state 1573 shifts to the storage state. During the countdown period 1521, a certain numerical value, clock, or index may be displayed on the user interface of the imaging control unit 1405, or an index may be displayed on the imaging apparatus side I/F 1403. The operator confirms the transition to the storage state. Referring to FIG. 15B, the output unit 1402c outputs depression information of the signal 1571 of the first switch 1401a of the exposure switch 1401 and the depression information of a signal 1572 of the second switch 1401b thereof. In this case, after an X-ray generator preparation period 1520 has elapsed since the time of depression, the X-ray generator state 1577 shifts to the X-ray emission ready state, and the X-ray generator emits X-ray. The radiant ray detector 1304 reads an X-ray image when a storage period timeout or X-ray detection occurs. Pressing in advance the first switch 1401a before the radiant ray detector 1304 shifts to the storage state enables the X-ray generator state 1577 to immediately shift to the X-ray emission state, shortening the cycle time.

Figure 16A:
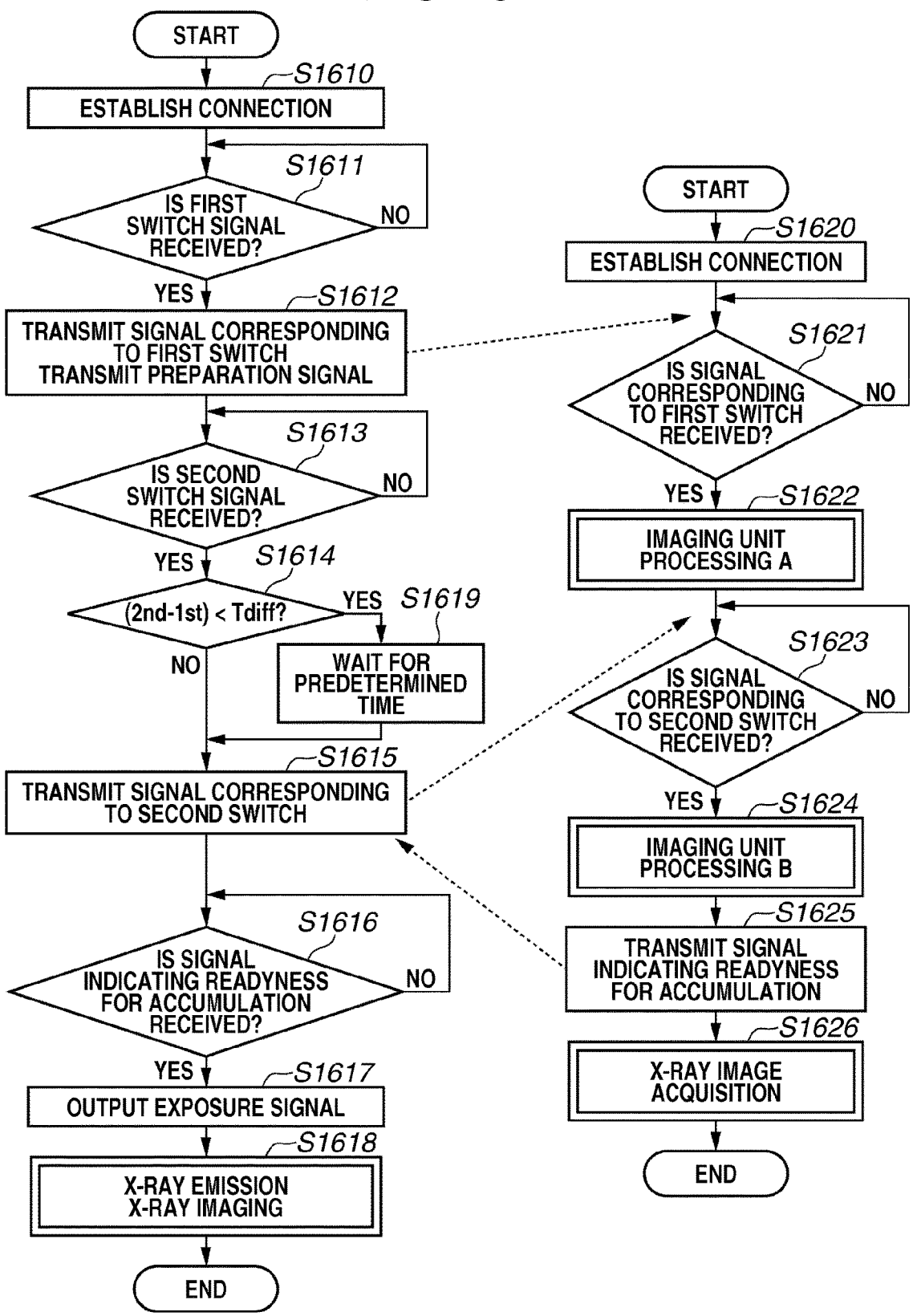
FIG. 16A is a flowchart illustrating a flow of control by an X-ray imaging system according to an exemplary embodiment.

The following describes the flow of processing according to an exemplary embodiment, with reference to FIG. 16. FIG. 16A is a flowchart illustrating main control performed by the control unit of the generation apparatus side I/F 1202. Although the processing will be described below as processing performed by the radiation imaging system illustrated in FIG. 1, processing performed by the radiation imaging system according other exemplary embodiments is performed in a similar way. The exemplary embodiment illustrated in FIG. 16 will be described below on the premise that the exposure switch 101 is a 2-step switch including the first switch 101a and the second switch 101b.

In step 1610, the control unit 102b establishes connection (first connection) between the generation apparatus side I/F 102 capable of acquiring a signal from the exposure switch 101 and the radiant ray detector 104. The control unit 102b establishes connection (second connection) by the connection unit 130 between the generation apparatus side I/F 102 capable of acquiring a signal from the exposure switch 101 and the radiant ray generation apparatus 108. In the case of wired connection, the establishment of connection includes at least one of the physical connection of a connector and the formation of an electrical signal transmission path. In the case of wireless connection, the establishment of connection includes processing performed by the acquisition unit 102a and the output unit 102c serving as wireless communication units. The performed processing makes command and information exchange with the connection unit possible on the side of the radiant ray generation apparatus 108.

In step 1611, the acquisition unit 102a acquires the first signal indicating that the first switch 101a (first switch) of the exposure switch 101 is pressed. Accordingly, the acquisition unit 102a detects the depression of the first switch 101a. If the first signal cannot be acquired, the acquisition unit 102a waits for a signal indicating that the first switch 101a of the exposure switch 101 is pressed. The acquisition unit 102a further stores in a storage unit the time at which the first switch 101a of the exposure switch 101 is pressed and the first switch signal is received.

In step 1612, the output unit 102c outputs a signal (signal corresponding to first switch) for shifting the radiant ray detector 104 to the radiation detectable state in response to the first signal of the exposure switch 101.

The output unit 102c further outputs to the radiant ray generation apparatus 108 a preparation signal for instructing preparation processing for shifting to the ready state for radiation generation. The control unit 102b generates the preparation signal upon depression of the first switch 101a.

In step 1613, the acquisition unit 102a acquires a signal (first signal) indicating that the second switch 101b of the exposure switch 101 is pressed. The acquisition unit 102a detects the depression of the second switch 101b. The acquisition unit 102a further stores in the storage unit the time at which the second switch 101b of the exposure switch 101 is pressed and the second switch signal is received.

In step 1614, the control unit 102b controls the signal output timing according to a difference between detected time of depressions. The control unit 102b reads the time of depression of the second switch 101b and the time of depression of the first switch 101a from the storage unit, calculates a difference between the times of two depressions, and determines whether the difference is smaller than a threshold value Tdiff. For example, when the first switch 101a and the second switch 101b are pressed at approximately the same time as described below, the time difference is considered to be smaller than the threshold value Tdiff. In this case (YES in step 1614), then in step 1619, the control unit 102b waits for a predetermined time period based on the time difference. Thus, if the difference between the time of depression of the first switch 101a and the time of second switch 101b is smaller than the specific threshold value Tdiff, the control unit 102b delays the signal output timing by a specific time duration.

This provides a wait time corresponding to the rotor-up processing performed by the radiant ray generation apparatus 108 upon depression of the first switch 101a. Providing this wait time shortens the time period of the storage state of the radiant ray detector 104, improving the image quality of the radiographic image.

The wait time is determined by the control unit 102b as a time period obtained by subtracting the time taken for the initialization processing of the radiant ray detector 104 from the time taken for the rotor-up processing. The time taken for signal transmission may be further subtracted from this time. Alternatively, Tdiff may be defined as the time taken for the rotor-up processing, and the wait time may be determined based on such time.

In step 1615, the output unit 102c outputs a signal for shifting the radiant ray detector 104a to the radiation detectable state upon depression of the exposure switch 101 and control by the control unit 102b. After waiting for a required time, the output unit 102c transmits a signal corresponding to the second switch to the radiant ray detector 104 in response to an output instruction from the control unit 102b.

Since the threshold value Tdiff and the wait time depend on the radiant ray generation apparatus 108 which is paired with the radiant ray detector 104, these values are desirably prestored in the storage unit to enable imaging when connecting the radiant ray detector 104 with a plurality of radiant ray generation apparatuses 108. For example, the threshold value Tdiff and the wait time are stored for each radiant ray generation apparatus 108. Such storage unit is provided in the generation apparatus side I/F 102 (radiation imaging control apparatus) connected to the radiant ray generation apparatus 108, or in the imaging apparatus side I/F 103. Alternatively, these values are stored in a management server which integrally manages a plurality of radiant ray detectors 104 and the radiant ray generation apparatuses 108, and acquired by the generation apparatus side I/F 102 or the imaging apparatus side I/F 103 depending on the radiant ray generation apparatus 108 to be connected.

Further, since the wait time also varies depending on the initialization processing time of the radiant ray detector 104, the wait time can be stored in the storage unit for each pair of the radiant ray generation apparatus 108 and the radiant ray detector 104. Connecting the radiant ray generation control apparatus and the radiant ray generation apparatus 108 by cable is useful because it becomes less necessary to take the delay into consideration.

The generation apparatus side I/F 102 (radiant ray generation control apparatus) and the radiant ray generation apparatus 108 can be connected by using a connection method based on a connection format in which signal delays and defects are permitted, such as the wireless LAN. In such a case, further, the wait time can be set taking signal delays into consideration.

When the difference between the time of depressions of the first switch 101a and the time of the second switch 102b is determined to be larger than the specific threshold value Tdiff, the output unit 102c outputs a signal corresponding to the second switch upon depression of the second switch 102b.

In step 1616, the acquisition unit 102a acquires the second signal indicating the driving state of the radiant ray detector 104 from the radiant ray detector 104 via the first connection.

In step 1617, the output unit 102c functioning as a wireless communication unit outputs a specific signal (exposure signal) to the radiant ray generation apparatus 108 via the second connection upon acquisition of the signal (first signal) and the second signal generated upon depression of the second switch 101b. The specific signal is a signal for instructing the radiant ray generation apparatus 108 to carry out radiation emission, and is generated by the control unit 102b upon depression of the second switch 101b. The signal generated upon depression of second switch can be output as it is.

In step 1618, the control unit 1081 of the radiant ray generation apparatus 108 controls the radiation source 107 of the radiant ray generation apparatus 108 to generate radiant ray upon acquisition of the specific signal.

The following describes processing performed by the imaging apparatus corresponding to processing performed by the radiant ray generation apparatus 108.

In step 1620, the imaging apparatus establishes connection with the radiant ray detector 104, the imaging control unit 105, the imaging apparatus side I/F 103, and the generation apparatus side I/F 102. As described in the exemplary embodiment illustrated in FIG. 12, the connection between the radiant ray detector 104 and the imaging control unit 105 is established when the wireless communication unit using infrared ray provided in imaging apparatus side I/F 103 transmits wireless communication parameters to the radiant ray detector 104 in response to a request from the radiant ray detector 104.

In step 1621, the wireless communication unit of the radiant ray detector 104 waits for reception of a signal corresponding to the first switch 101a.

In step 1622, the detector control unit of the radiant ray detector 104 performs the initialization processing (imaging unit processing A) as required upon reception of the first switch signal. This processing corresponds, for example, to the initialization processing illustrated in the timing chart in FIG. 11A. This processing is omitted if the initialization processing is not required when the radiant ray detector 104 shifts from the idle state to the storage state.

In step 1623, the wireless communication unit of the radiant ray detector 104 waits for reception of a signal corresponding to the second switch 101b.

In step 1624, the detector control unit of the radiant ray detector 104 performs the initialization processing (imaging unit processing A) as required. This processing corresponds, for example, to the initialization processing illustrated in the timing chart in FIG. 5B. This processing is omitted if the initialization processing is not required when the radiant ray detector 104 shifts from the idle state to the storage state.

In step 1625, the wireless communication unit of the radiant ray detector 104 transmits the signal indicating readyness for accumulation (second signal) to the generation apparatus side I/F 102.

In step 1626, the radiant ray detector 104 which has shifted to the storage state detects radiant ray to acquire image data.

Figure 16B:
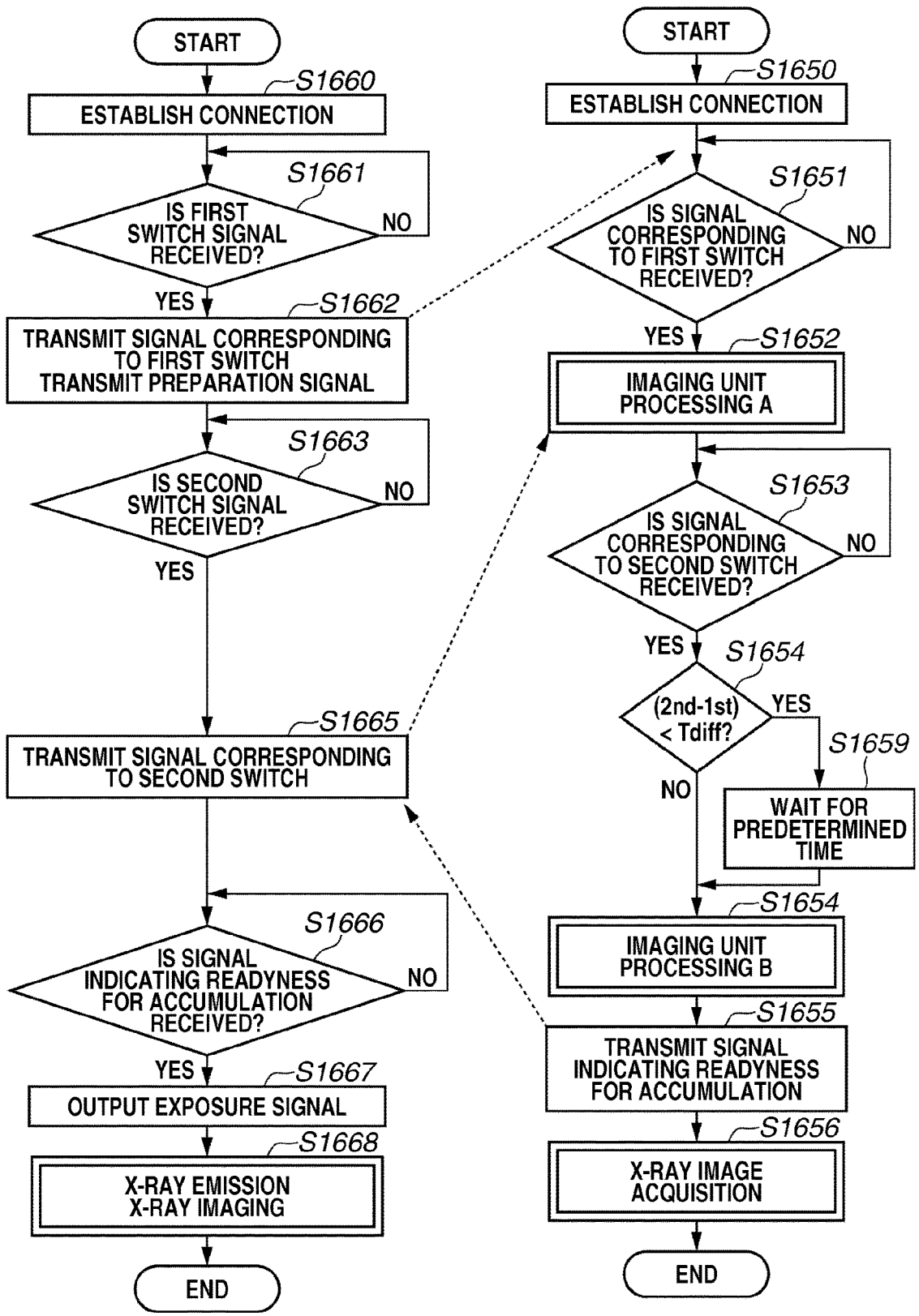
FIG. 16B is a flowchart illustrating a flow of control by an X-ray imaging system according to still another exemplary embodiment.

FIG. 16B is a flowchart illustrating main control performed by the control unit of the imaging apparatus side I/F 103. As for steps in which similar processing to steps illustrated in FIG. 16A is performed, redundant descriptions will be omitted.

In step 1665, the output unit 102c transmits the signal corresponding to the second switch signal to the imaging apparatus.

In step 1654, the control unit 102c of the imaging apparatus side I/F 103 calculates a time interval between the reception timing of a signal corresponding to the first switch signal and the reception timing of a signal corresponding to the second switch signal, and determines whether the calculated time interval is smaller than the threshold value Tdiff. In consideration of signal transmission, the threshold value Tdiff may be different from Tdiff illustrated in FIG. 16A. If the time interval is determined to be smaller than Tdiff (YES in step 1654), then in step 1659, the control unit 102c provides a wait time for delaying the transmission of the signal indicating readyness for accumulation (second signal) by the control unit 102c.

This processing enables shortening the storage time period to improve the image quality of a radiographic image acquired through synchronous imaging.

The following describes processing performed when an operator 100 presses the first switch 101a and the second switch 101b at approximately the same time, with reference to a timing chart illustrated in FIG. 17. For convenience, the following describes the radiation imaging system according to the exemplary embodiment illustrated in FIG. 1 in which only as to the switching unit, a 2-step exposure switch 1701 is employed. FIG. 17A is a timing chart when the generation apparatus side I/F 102 simply transmits a first switch signal 1771 and a second switch signal 1772 to the imaging apparatus side I/F 103 and the radiant ray generation apparatus 108. The first switch signal 1771 and the second switch signal 1772 transition at approximately the same time. Although the imaging unit driving state 1773 shifts to the storage state in a short time, a preparation period, such as the rotor-up processing of, occurs about one second in the X-ray generator state. Depending on a method for driving the radiant ray detector 104, the storage enable time approximately ends in this preparation period in the imaging unit driving state 2173, so that during the radiation emission period of the radiant ray generation apparatus 108, the radiant ray detector 1773 cannot shift to the image read state to perform correct image formation. To solve this problem, referring to FIG. 17A, by extending the storage time period to be longer than a predetermined time, invalid radiation emission due to the end of the exposure storage time period can be prevented.

This problem can be solved also by providing a delay time when the generation apparatus side I/F 102 transmits the second switch signal 1772 and a signal corresponding to the second switch to the imaging apparatus side I/F 103.

Figure 17B:
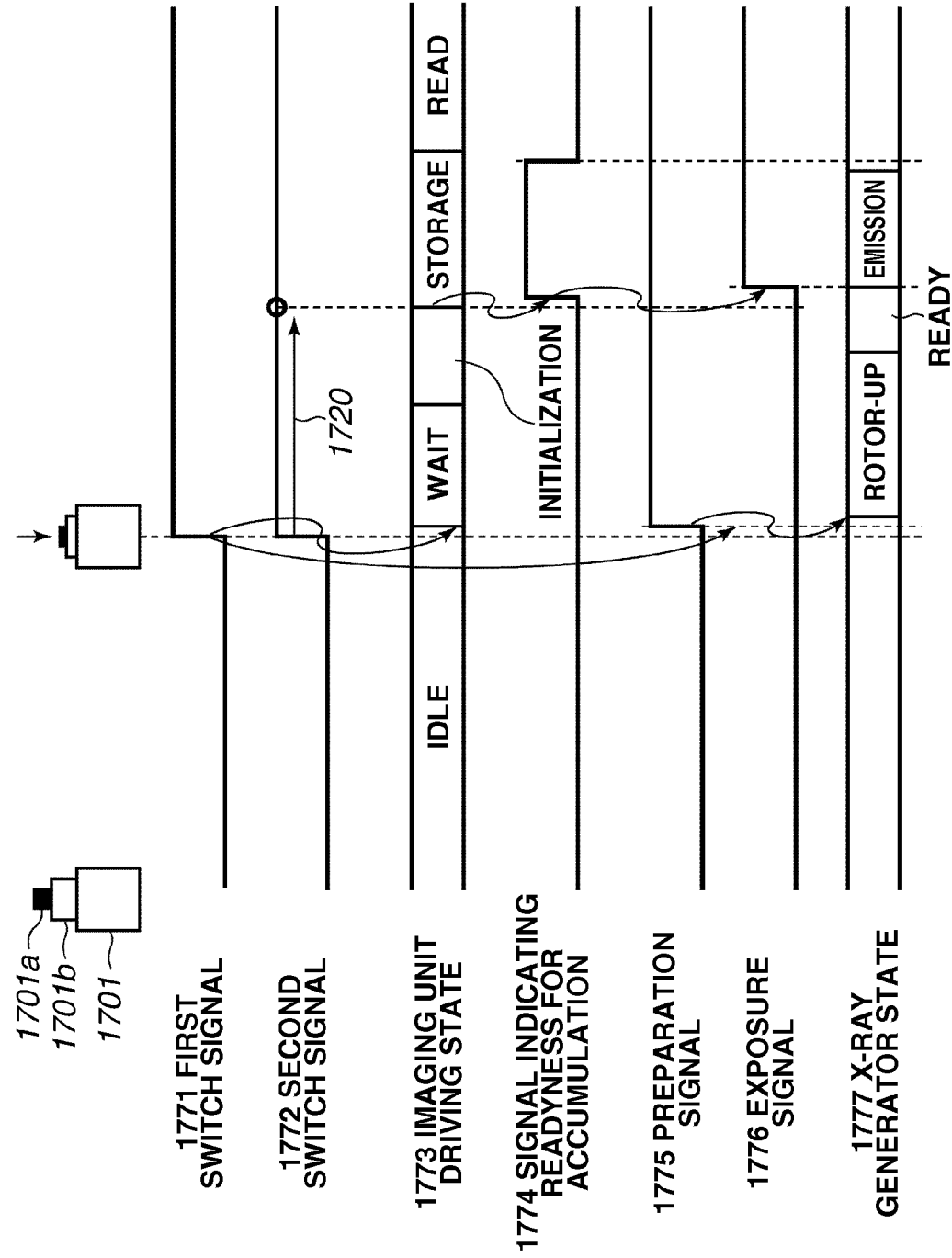
FIG. 17B is a timing chart illustrating control according to still another exemplary embodiment.

The following describes another solution for this problem with reference to a timing chart illustrated in FIG. 17B. As illustrated in FIG. 17B, the generation apparatus side I/F 102 transmits the relevant signals to the imaging apparatus side I/F 103 to provide in the radiant ray detector 104 a timing difference between the processing for the first switch signal and the processing for the second switch signal 1772 of a predetermined time period. This wait processing for a predetermined time period corresponds to the rotor-up time of the radiant ray generation apparatus 108, and is defined for each radiant ray generation apparatus 108. During the wait processing, the radiant ray detector 104 may be in the storage state or repeat the storage state and the initialization processing as in the idle state. As illustrated in FIG. 17B, when the radiant ray detector 104 requires the initialization processing when a state transitions from the idle state to the storage state, will wait for a time period obtained by subtracting the time taken for the initialization processing from a predetermined time taken for the rotor-up processing. In this case, the radiant ray detector 104 shifts from the idle state to the wait state first, performs the initialization processing, and then shifts to the storage state to further shorten the duration of the storage state, providing an advantage in image quality. In this case, it is also possible that a radiant ray generation apparatus preparation period, such as the period of the rotor-up processing of the radiant ray generation apparatus 108, is preregistered in the radiant ray detector 104, and that the generation apparatus side I/F 102 rejects the signal corresponding to the second switch from the time when it outputs the signal corresponding to the first switch until the time when the relevant preparation period (preset based on the arrival time) ends or when the relevant preparation period reduced by the imaging unit drive initialization time ends. In this case, after reception of the second switch signal 1772, the imaging apparatus side I/F 103 waits for a preparation period 1720 and then returns a signal indicating readyness for accumulation 1774 to the generation apparatus side I/F 102, thus achieving synchronization.

Although, in the above-described exemplary embodiment, both the signal corresponding to the first switch and the signal corresponding to the second switch are transmitted to the radiant ray detector 104, this condition is not a prerequisite. The exemplary embodiment is applicable even when either one of the signals is transmitted thereto. When the signal corresponding to the first switch is not present, it is only necessary to, after reception of the signal corresponding to the second switch, start the processing which is conventionally performed upon reception of the signal corresponding to the first switch. When only the signal corresponding to the first switch is received, the method for driving the radiant ray detector 104 is limited. However, after reception of the signal corresponding to the first switch, the radiant ray detector 104 may wait using a driving method which allows constant radiation storage and then perform radiation detection.

The above-described exemplary embodiment premises that the rotor-up processing on the side of the radiant ray generation apparatus 108 takes longer time than the initialization processing of the radiant ray detector 104. If the rotor-up processing of the radiant ray generation apparatus 108 takes shorter time than the initialization processing, the control unit 102b first performs control to output, upon depression of the first switch 101a, a signal for instructing to shift to the storage state, to the radiant ray detector 104 via the output unit 102c. The control unit 102b determines whether the time difference between the depression of the first switch 101a and the depression of the second switch 101b is smaller than the threshold value. In a case where the time difference is determined to be smaller than the threshold value, if the control unit 102b waits for a predetermined time period and then performs control to output the preparation signal to the radiant ray generation apparatus 108, the wait time of the radiant ray generation apparatus 108 can be shortened. As a radiant ray generation apparatus having a very short rotor-up time, a radiant ray generation apparatus having a transmission type radiation source can be employed.

Figure 18A:
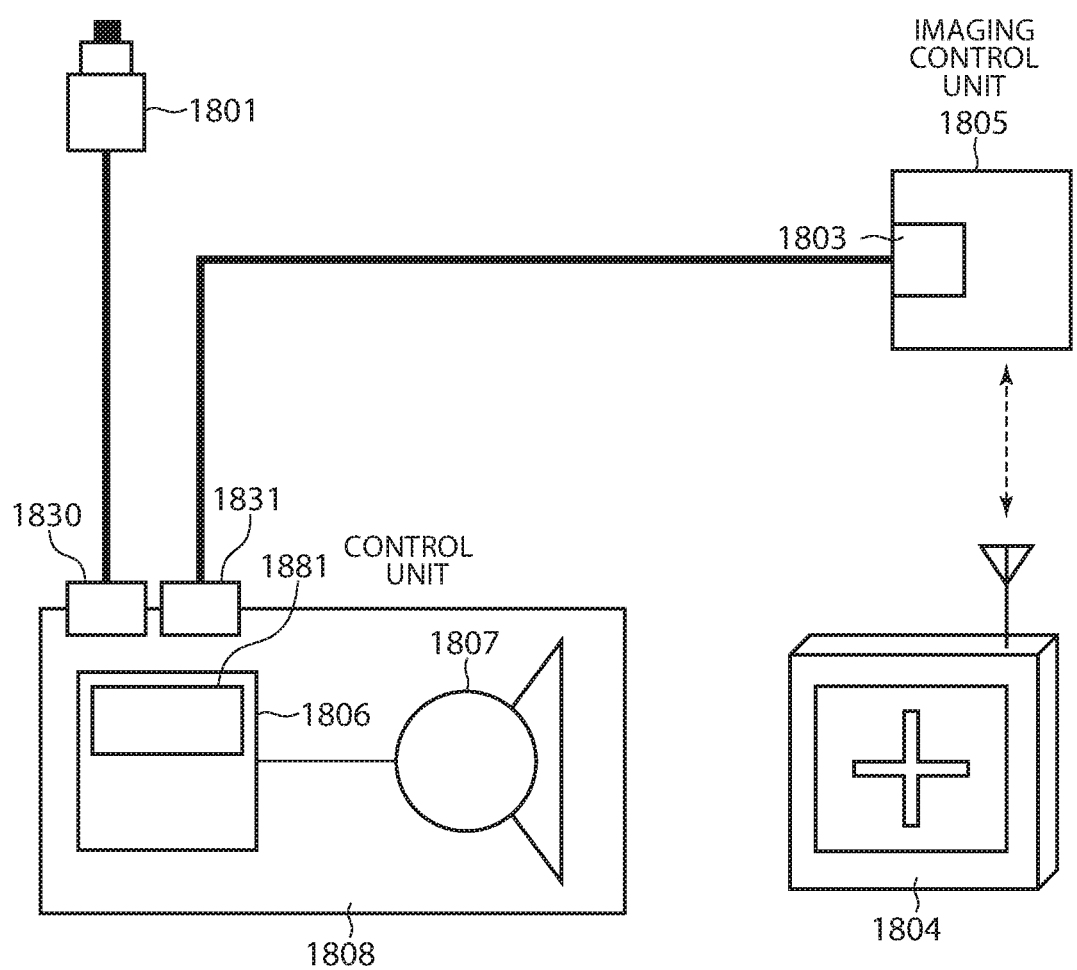
FIG. 18A is a block diagram illustrating an X-ray imaging system when a command communication interface is provided on an X-ray generator.

The following describes an example in which the imaging apparatus side I/F is configured in the imaging control unit or the radiant ray detector, with reference to FIG. 18. FIG. 18A illustrate an exemplary embodiment in which the function of an imaging apparatus side I/F 1803 is included in an imaging control unit 1805. The generation apparatus side I/F 1803 and the radiant ray generation apparatus 1808 are connected by cable via a connection unit 1831. In the exemplary embodiment illustrated in FIG. 18B, the imaging apparatus side I/F 1803 is included in a radiant ray detector 1804, and the radiant ray detector 1804 and the radiant ray generation apparatus 1808 are wirelessly connected. For wired connection, Ethernet (registered trademark) or a general-purpose interface, such as the RS232C and USB, is applicable. For wireless connection, the wireless LAN standard, Bluetooth (registered trademark), or IrDA communication is applicable. With this method, a signal equivalent to an exposure switch 1801 or timing information having additional information is operated by using command communication. The command communication refers to a communication method in which, when transmission is carried out on an identical transmission medium, an electrical signal which temporally varies with a predetermined pattern is separated and clipped as a command based on a specific rule. In the RS232C, based on a rule of voltage signal level transition, such as the start bit and stop bit, a specific command is extracted from the signal level. This communication method, called serial communication, enables information exchange with the radiant ray generation apparatus 1808, the imaging control unit 1805 on the side of the radiant ray detector 1804, or the radiant ray detector 1804 on the same communication medium. The information to be exchanged includes a synchronization timing signal related to X-ray imaging, a setting condition related to X-ray generation at the time of imaging, and operation record information about completed X-ray generation. For example, when condition settings at the time of imaging have been registered in the user interface of the imaging control unit 1805, in this connection format, the setting information can be transmitted as a command from the imaging control unit 1805 to the radiant ray generation apparatus 1808 directly or via the radiant ray detector 1804. This enables unified management of information about X-ray condition settings between the radiant ray generation apparatus 1808 and the radiant ray detector 1804. Further, in the connection format, the operation information after X-ray emission, such as measurement information about actual X-ray emission (information about tube voltage, tube current, and exposure time), can be transmitted as a command from the radiant ray generation apparatus 1808 to the imaging control unit 1805 or the radiant ray detector 1804. In particular, by receiving the operation information immediately after completion of X-ray emission via the radiant ray detector 1804, an X-ray image can be linked with the operation information and, depending on the case, with patient information from the imaging control unit 1805, so that essential information about the X-ray image can be linked in the early stage. This method enables reducing a risk of wrong acquisition caused for some reason. By this method, image management can be free from confusion regarding consistency between the patient information and the image even if depending on the case, the image is once stored in the radiant ray detector 1804 and then transmitted to the imaging control unit 1805.

Figure 19:
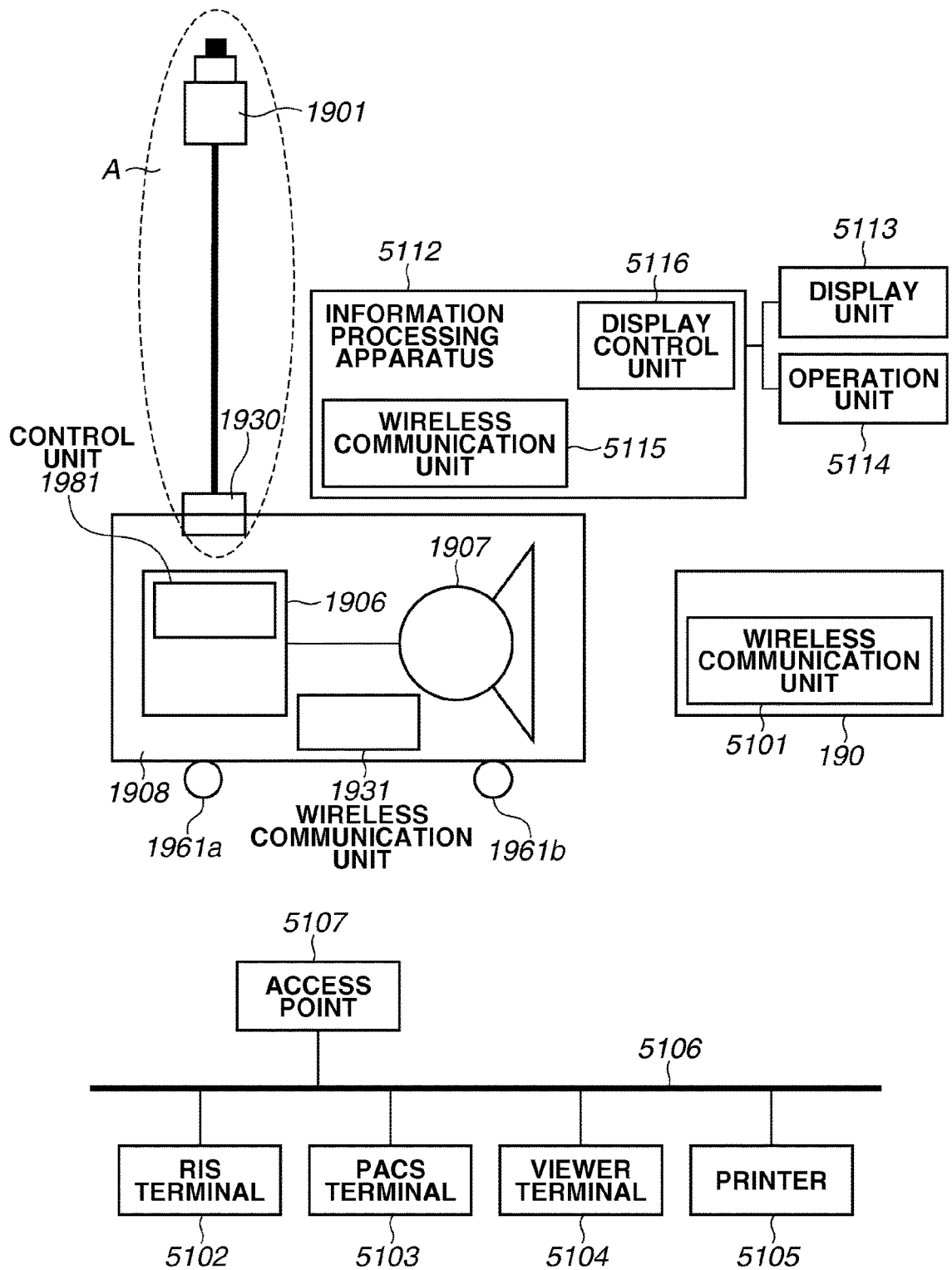
FIG. 19 is a block diagram illustrating a mobile radiation imaging system according to an exemplary embodiment.

The following describes an exemplary embodiment of the present invention including a mobile radiant ray generation apparatus, with reference to FIG. 19. For elements equivalent to those in the above-described exemplary embodiments, redundant descriptions will be omitted. A radiant ray generation apparatus 1908 is made movable, for example, by using moving members 1961a and 1961b composed of wheels and so on. The radiant ray generation apparatus 1908 is used for a doctor's round of visits and can be moved between sickrooms and an operating room in a hospital. A wireless communication unit 1931 can be provided in a radiant ray generation apparatus 1908. The wireless communication unit 1931 enables exchange of imaging conditions and the operation information via a wireless communication unit 5101 of the radiant ray detector 1901 and an access point 5107.

The mobile radiant ray generation apparatus 1908 is provided with an information processing apparatus 5112 which is one form of the imaging control unit. A display unit 5113 and an operation unit 5114 are connected to the information processing apparatus 5112. The operator can operate the screen displayed on the display unit 5113 via the operation unit 5114. This enables imaging condition setting, target patient information selection, captured image reception, and image transmission to a server. The screen displayed on the display unit 5113 is controlled by the display control unit 5116. Information exchange with an external apparatus is performed, for example, by a wireless communication unit 5115.

When the information processing apparatus 5112 is integrated with the radiant ray generation apparatus 1908, i.e., detachably attaching is not taken into consideration, wired communication enables improving the reliability of the radiation imaging system. When the information processing apparatus 5112 is composed of, for example, a notebook personal computer (PC) or a tablet type terminal, wireless communication is useful.

The switching unit A, having no unit for synchronizing with the radiant ray detector 190, is connected to the radiant ray generation apparatus 1908. However, instead of the switching unit A, the switching unit B having the generation apparatus side I/F 102 as illustrated in FIG. 1 can be connected thereto. If the switching unit A is connected, when the radiant ray detector 190 detects radiant ray generated by the radiant ray generation apparatus 1908, it shifts to the storage state to acquire image data. If the switching unit B is connected, imaging is performed by the radiant ray detector 104 synchronized with the radiant ray generation apparatus 1908 under control of the information processing apparatus 5112. Such imaging control changeover is performed under control of the information processing apparatus 5112. An image transmitted from the information processing apparatus 5112 via the access point 5107 is stored in the server, can be viewed from a Picture Archiving and Communication Systems (PACS) terminal 5103 and a viewer terminal 5104, and output to paper medium or a film via a printer 5105 as required. The information processing apparatus 5112 receives an imaging order from a Radiology Information System (RIS) and then performs the imaging according to the order.

Figure 20:
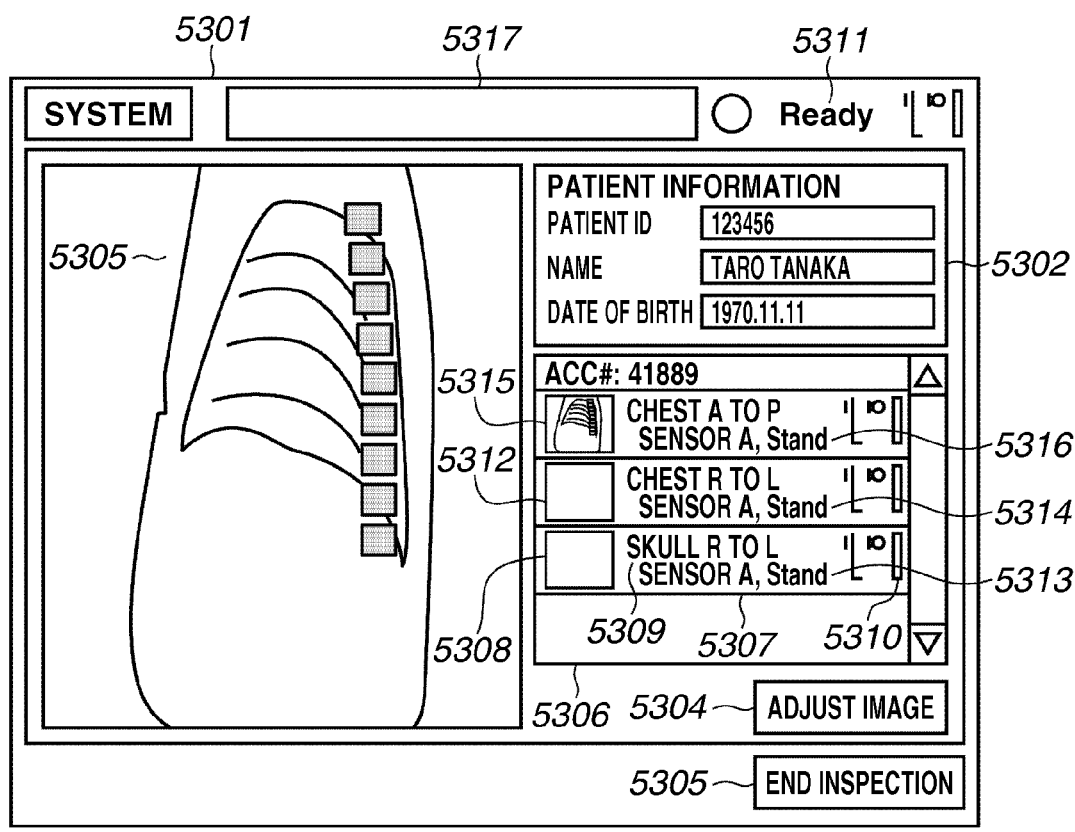
FIG. 20 illustrates an example of an imaging graphic user interface (GUI) screen displayed on a display unit of an X-ray imaging system.

The following describes the screen displayed on the display unit 5113 connected to the information processing apparatus 5112 functioning as the imaging control unit 105, with reference to FIG. 20. Display control of the display screen is performed by the display control unit 5116.

FIG. 20 illustrates an example of an imaging screen 5301 displayed on the display unit 5113 under control of the display control unit 5116. The screen 5301 includes a subject information display area 5302 displaying subject information, a preview image display area 5303 displaying a captured image, an image adjustment button 5304 for instructing adjustment of image processing parameters of the captured image currently being previewed, a test end button 5305 for instructing to end a test, and a test order display area 5306 displaying information about the test order currently being executed. The test order display area 5306 includes a plurality of imaging protocol buttons 5307.

Each imaging protocol button 5307 includes a thumbnail display area 5308 displaying a thumbnail of captured images, a name display area 5309 displaying names of captured portions, a sensor type display area 5310 displaying sensor type information, such as upright position and recumbent position, and an imaging environment information display area 5313 displaying the sensor type and imaging posture. Each imaging protocol button 5307 also displays the captured state (currently being previewed), the imaging preparation state, and the imaging ready state. The screen 5301 further includes a sensor status display area 5311 displaying the sensor state related to the imaging protocol currently being executed. Although the screen 5301 displays characters as status display, the display control unit 5112 may change the color of buttons and perform animation display and other GUI-based status display, providing the user with information in an intuitive way.

The display area 5317 displays various statuses of the radiation imaging system according to the above-described exemplary embodiments. The display area 5317 displays various information about the radiation imaging system, for example, whether the radiant ray detector 104 is in the storage state, whether the connected switching unit is applicable to synchronous imaging (as in the exemplary embodiment illustrating FIG. 1), whether the switching unit is by cable connected or wirelessly connected, how many switches are connected, and whether other switches are mounted on the exposure switch (as in the exemplary embodiment illustrated in FIG. 13). Thus, the user can grasp information about the radiation imaging system in an integrated way.

Any desired combinations of the above-described exemplary embodiments are also included in the present invention.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

What is claimed is:

1. An X-ray generation control apparatus comprising:
an exposure switch;
a first connection unit connected to an X-ray detector and configured to receive a second signal from the X-ray detector;
a second connection unit connected to an X-ray generation apparatus and configured to transmit a specific signal;
a memory storing instructions; and
one or more processors that, upon execution of the instructions, are configured to operate as:
an acquisition unit configured to acquire a first signal indicating that the exposure switch to instruct radiation emission is pressed; and
a control unit configured to output the specific signal via the second connection unit in response to acquisition of the first signal and reception of the second signal,
wherein the specific signal is either the first signal or the second signal.

2. The X-ray generation control apparatus according to claim 1,
wherein the first connection unit is detachably connected to the X-ray detector, and
wherein the second connection unit is detachably connected to the X-ray generation apparatus.

3. The X-ray generation control apparatus according to claim 1, wherein the second connection unit comprises a connector to wired connection.

4. The X-ray generation control apparatus according to claim 1, further comprising a relaying portion, wherein the second connection unit is connected to the relaying portion for relaying connection and transmitting the specific signal to the X-ray generation apparatus.

5. The X-ray generation control apparatus according to claim 1, wherein the control unit is configured to output the first signal as the specific signal via the second connection unit in response to reception of the second signal indicating a driving state of the X-ray generation apparatus.

6. The X-ray generation control apparatus according to claim 1, wherein the control unit is configured to output a third signal for requesting information on a driving state of the X-ray detector via the first connection unit in response to reception of the first signal.

7. The X-ray generation control apparatus according to claim 1, wherein the second signal is a signal indicating whether the X-ray detector is being capable of imaging.

8. The X-ray generation control apparatus according to claim 1, wherein the control unit is configured to output the specific signal in order to terminate X-ray emission from the X-ray generation apparatus in accordance with the second signal from the X-ray detector.

9. The X-ray generation control apparatus according to claim 1, wherein the control unit is configured to output the specific signal while the exposure switch is pressed, and terminate output of the specific signal in accordance with the second signal from the X-ray detector.

10. An X-ray imaging system comprising:
an X-ray generation apparatus configured to generate an X-ray;
an X-ray detector configured to detect the X-ray and acquire an X-ray image;
an image control unit; and
an X-ray generation control apparatus including:
an exposure switch;
a first connection unit connected to the X-ray detector and configured to receive a second signal from the X-ray detector;
a second connection unit connected to the X-ray generation apparatus and configured to transmit a specific signal;
a memory storing instructions; and
one or more processors that, upon execution of the instructions, are configured to operate as:
an acquisition unit configured to acquire a first signal indicating that the exposure switch to instruct radiation emission is pressed; and
a control unit configured to output the specific signal via the second connection unit in response to acquisition of the first signal and reception of the second signal,
wherein the specific signal is either the first signal or the second signal,
wherein the X-ray generation apparatus is controlled by the X-ray generation control apparatus, and
the image control unit is configured to control the X-ray generation control apparatus and the X-ray detector.

11. A control method comprising:
connecting a first connection unit of an exposure switch to an X-ray detector, the first connection unit configured to receive a second signal from the X-ray detector;
connecting a second connection unit of the exposure switch to an X-ray generation apparatus, the second connection unit configured to transmit a specific signal;
acquiring a first signal indicating that the exposure switch is pressed; and
controlling the X-ray generation apparatus by outputting the specific signal via the second connection unit to the X-ray generation apparatus in response to acquisition of the first signal and reception of the second signal,
wherein the specific signal is either the first signal or the second signal.

* * * * *